United States Patent [19]
Yamaguchi et al.

[11] Patent Number: 5,092,340
[45] Date of Patent: Mar. 3, 1992

[54] ORGANISM SIGNAL MEASURING APPARATUS

[75] Inventors: Keiji Yamaguchi; Takafumi Go; Tadashi Fujii, all of Fuji; Toshinori Hirano, Kawasaki, all of Japan

[73] Assignee: Terumo Kabushiki Kaisha, Tokyo, Japan

[21] Appl. No.: 347,893

[22] PCT Filed: Oct. 16, 1987

[86] PCT No.: PCT/JP87/00791
§ 371 Date: Apr. 12, 1989
§ 102(e) Date: Apr. 12, 1989

[87] PCT Pub. No.: WO88/02617
PCT Pub. Date: Apr. 21, 1988

[30] Foreign Application Priority Data
Oct. 17, 1986 [JP] Japan ............... 61-245195

[51] Int. Cl.$^5$ .............................. A61B 5/402
[52] U.S. Cl. ...................... 128/696; 128/704; 364/413.06
[58] Field of Search ............... 128/696, 702, 703, 704; 364/413.06

[56] References Cited
U.S. PATENT DOCUMENTS
3,903,874  9/1975  Shakespeare .

FOREIGN PATENT DOCUMENTS
7168640  10/1982  Japan .
61-56633  3/1986   Japan .
WO81/02832 3/1981 PCT Int'l Appl. .

OTHER PUBLICATIONS
J. Fraden et al.: "QRS wave detection", Medical & Biological Eng & Comp., vol. 18, No. 2, Mar. 1980, pp. 125–132.
J. Qrum: "Der Cardioscatterhistograph–ein Gerat zur kontinuierlichen Anzeige quasiperiodischer Bio-Signale", Biomedizinische Technik, vol. 20, No. 5, Oct. 1975, pp. 192–198.
Supplemental European Search Report, The Hague, 12-01-89.

Primary Examiner—William E. Kamm
Assistant Examiner—Scott M. Getzow
Attorney, Agent, or Firm—Staas & Halsey

[57] ABSTRACT

An apparatus for achieving a long-term organism signal measurement, for example, an ECG waveform measurement includes measuring means (1) and input means (2) for setting and inputting organism signal analysis data in the measuring means (1). By supplying via the input means (2) organism signal analysis data unique to an organism to be measured into the measuring means (1), there is conducted a learning operation of the characteristics of the organism signals of the subject. Thereafter, the measurement and analysis of the organism signals are achieved for a long period of time by use of the measuring means (1). The measurement is accomplished after the characteristics of the organism signals of the subject are learned, and hence the reliability is increased. In addition, the realtime measurement and analysis are conducted by the measuring means (1) so as to store only abnormal waveforms, which facilitates the judgement thereof to be conducted by a doctor.

12 Claims, 19 Drawing Sheets

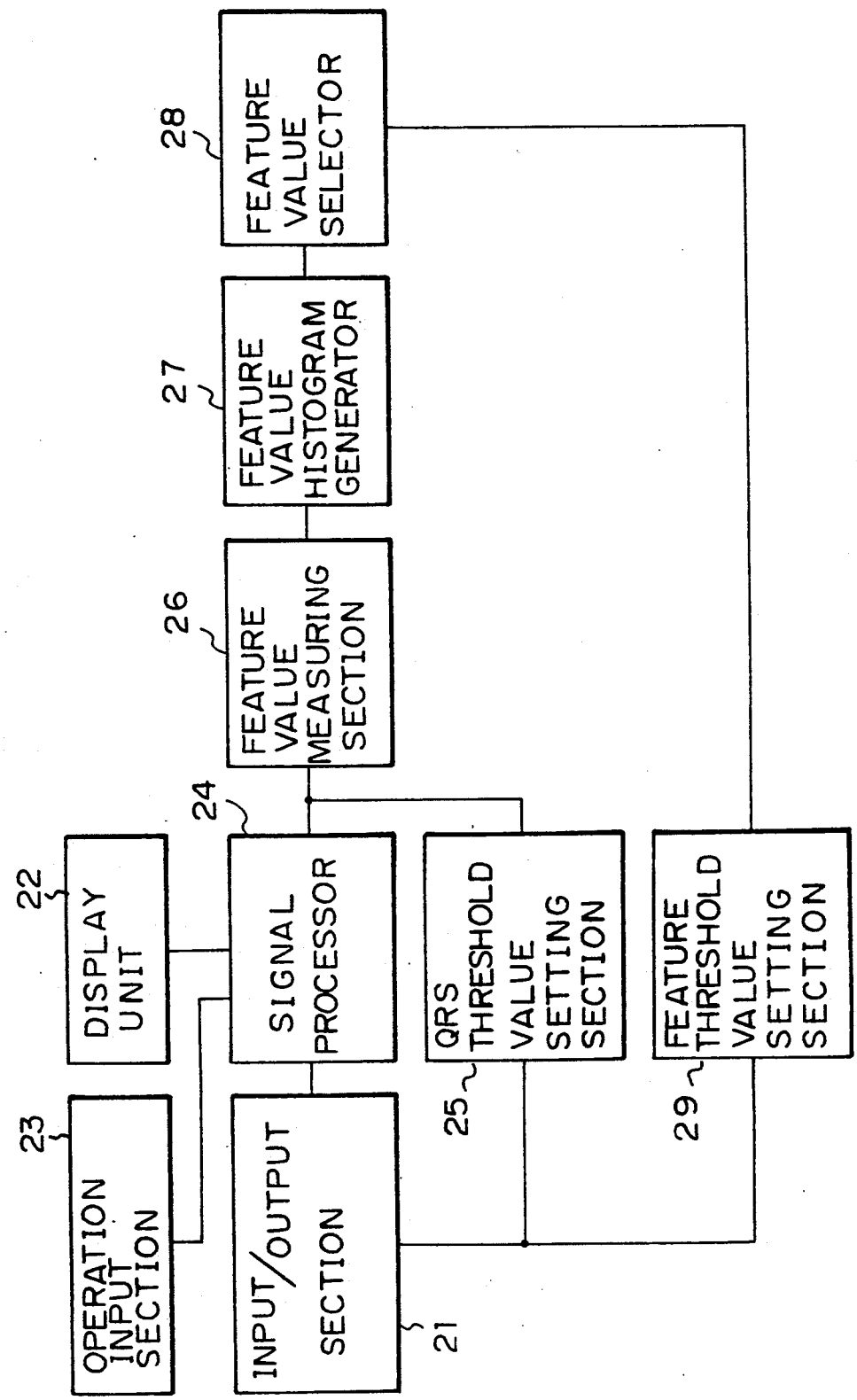

Fig. 12
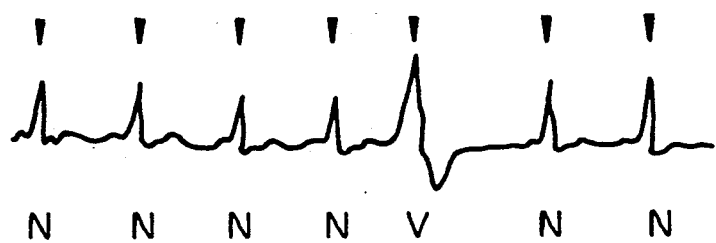
Fig. 13a
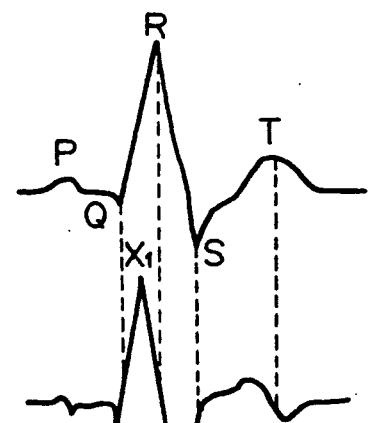
Fig. 13b
Fig. 13c
Fig. 14
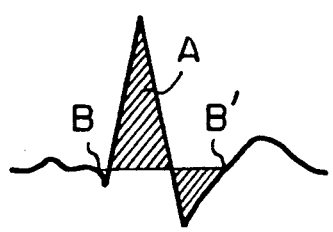
Fig. 15
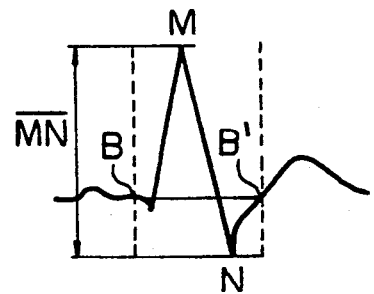

Fig. 27a
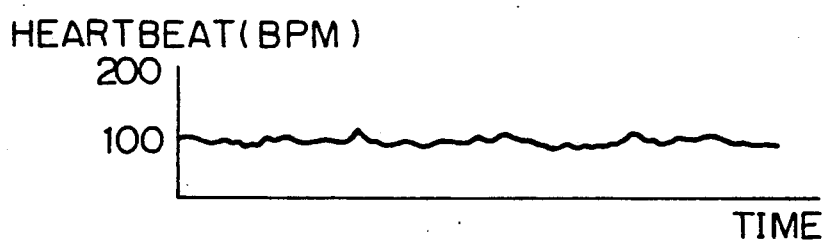
Fig. 27b
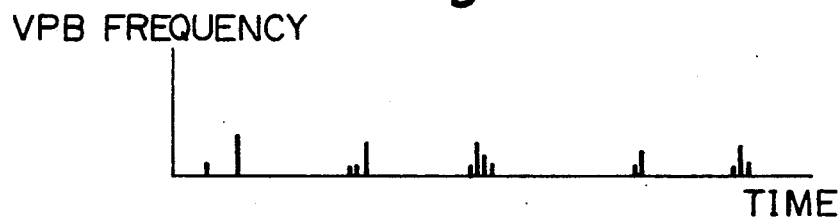
Fig. 27c
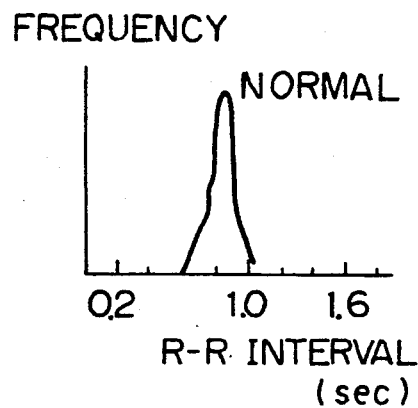
Fig. 27d
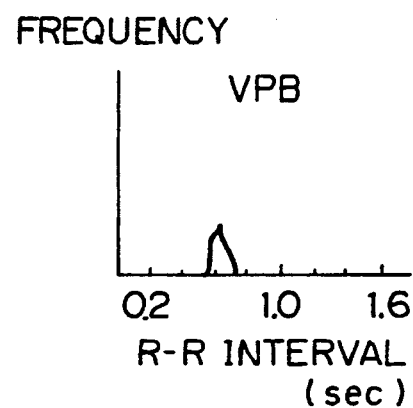
Fig. 27e
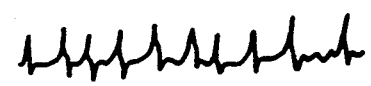

ORGANISM SIGNAL MEASURING APPARATUS

TECHNICAL FIELD

The present invention relates to an apparatus for measuring a signal from an organism or a living body for a predetermined period of time, and in particular, to a living body signal measuring apparatus for analyzing a signal from an organism in a realtime fashion.

BACKGROUND ART

In the field of medical treatment, a clinical examination measuring, for example, an electrocardiogram and a blood pressure measurement conducted as a daily job.

These examinations are ordinarily effected in quite a limited period of time in medical care institution such as a clinic or a hospital under control of a medical doctor or an examiner or inspector of an clinical check. However, there exist diseases which cannot be detected in the examination conducted in such a limited period of time.

For example, in a case of a temporary disorder of the heart or an arrhythmia, there does not necessarily appear an abnormal waveform in the electrocardiogram. Since an interval between appearances of such an abnormal waveform is great in many cases, the probability of the detection of such a disorder of the heart in a short period of time is decreased; in consequence, it is difficult in many cases to conduct a determinant diagnosis through an examination conducted requires a short period of time.

In this situation, for the detection of such diseases described above, there has been devised a method for measuring an electrocardiogram for a long period of time. According to this method, there is attained a long-term electrocardiogram or so-called Holter electrocardiogram such that for an entire day or 24 hours in the daily life, a portable electrocardiograph is kept attached on a portion of the body of a person as a subject so as to collect and to record electrocardiographic waveforms on a magnetic tape. The magnetic tape is thereafter read by use of a magnetic tape playback apparatus so as to reproduce the electrocardiographic waveforms, which are observed by an inspector such as a medical doctor to detect an abnormality, thereby conducting a diagnosis of disease such as a fugitive affection of the heart.

The electrocardiographic waveforms recorded on a magnetic tape are reproduced at a high speed due to the great volume thereof. Consequently, the inspector, for example, a medical doctor is required to conduct the diagnosis by visually checking such a great amount of electrocardiographic waveforms reproduced at a high speed, which imposes a hard load on the inspector.

As described above, in order to detect the arrhythmia which is a transistory disease and which appears at quite a rare occasion, the electrocardiographic waveforms collected in 24 hours are entirely reproduced so that analyzing the waveforms requires a long period of time, which requires many unnecessary jobs and which decreases the efficiency of the overall examination.

In order to eliminate the irrationality above, there has been adopted a method in which a magnetic tape containing a great volume of recorded waveforms is reproduced at a high speed (for example, at a speed which is 60 or 120 times the ordinary playback speed) such that the waveforms are automatically analyzed according to a predetermined method by the apparatus so as to display only the portions thereof judged to be abnormal as a result of the analysis, thereby enabling an inspector to examine the abnormal portions. However, since the magnetic tape undergoes a high-speed playback operation and data items of the electrocardiographic waveforms are inputted to the objective apparatus at a high speed, when it is desired to analyze the waveforms by use of, for example, a microcomputer, there cannot be afforded a sufficient time for the analysis, namely, it is difficult at the present stage of the technology to increase the accuracy of the analysis.

In order to overcome such a difficulty, there has been recently employed a method in which while the electrocardiographic waveforms are being gathered for a long period of time, an analysis of the waveforms are automatically achieved at the same time, namely, in a realtime manner such that portions of the waveforms judged to be abnormal as a result of the analysis are stored in a storage, for example, on a magnetic tape or in an IC memory so as to thereafter display these abnormal waveforms and analysis results by means of a display equipment installed at a location of a medical doctor and to effect a print-out operation thereof if necessary, which enables the doctor to confirm the results. In this method, as compared with the method above, a sufficient time can be afforded to conduct the analysis (60 or 120 times), which improves the accuracy of the analysis. In addition, only the ECG waveforms judged to be abnormal as result of the realtime ECG waveform analysis need only be stored in a storage such as a magnetic tape or an IC memory, it is possible to minimize the memory capacity and the weight of the apparatus, which therefore can be used as a portable apparatus.

In the realtime analysis of such a long-term measurement of electrocardiographic waveforms, all electrocardiographic waveforms appearing in 24 hours are not recorded, namely, there are stored only the waveforms judged to be abnormal as a result of the automatic analysis effected by the apparatus. In consequence, the waveforms judged to be normal by the automatic analysis are not stored, namely, even if there exists an abnormal waveform therein, the inspector cannot check such a waveform.

As described above, in the realtime analysis, it is quite important that any abnormal waveform can be detected; in addition, in order to minimize the examination job imposed on the inspector, it is also essential not to judge a normal waveform to be abnormal.

However, since the electrocardiographic waveforms include personal characteristics of the subject (differences in characteristics associated with respective persons), if the normality and the abnormality are automatically judged depending on a predetermined reference value, it is likely to increase the ratio of errors in the judgement.

In other words, when using electrocardiographic waveforms, a QRS portion where a level of the waveform signal greatly varies is detected so as to compute values of an area of the QRS, an amplitude (height) thereof, and the time index (index of the width) thereof, thereby judging to determine the normality or the abnormality depending on whether or not these values exceed the respective predetermined threshold values. Due to the difference between the threshold values of the individual persons, with any threshold values set in a case where the realtime analysis is effected while continuously measuring the signal for 24 hours, there remains a fear that the error ratio is increased in the judgement.

For example, an attempt has been made to correctly detect with a high accuracy an extrasystole associated with the ventricule which is most problematical in arrhythmia. In this case, the time index of the QRS portion (the index of the QRS width) is measured so as to determine the presence or absence of the extrasystole associated with the ventricule depending on whether or not the value of the measured index exceeds a predetermined threshold value. However, the threshold value as a boundary value between the normal value of the QRS with index and the abnormal value thereof cannot be absolutely determined, namely, the value varies depending on the individual cases; moreover, it has been well known that, for a person, the value changes during a day or between respective examination days. Namely, even when the same value is obtained for the QRS index, the value may be normal or abnormal depending on the individual cases. In consequence, it is impossible to uniquely fix the threshold value to judge the normal and abnormal cases without causing any errors.

SUMMARY OF INVENTION

It is therefore an object of the present invention to remove the disadvantages of the prior art technology and to provide a long-period living body signal measuring apparatus capable of effecting a long-term organism signal measurement such that a long-term analysis is achieved with a high precision with considerations of the individual characteristics of measured waveforms.

According to the present invention, the organism signal measuring apparatus includes measuring means for effecting a measurement and an analysis of an organism signal of a subject for a predetermined period to time so as to store the signal and to produce results of the measurement and the analysis, display means for displaying data outputted from said measuring means, and input means for inputting data for an organism signal analysis in said measuring means wherein by supplying in advance from said input means to said measuring means organism signal analysis data unique to a living body as a subject of the measurement so as to cause said measuring means to learn characteristics of the living body signal of the subject.

In addition, according to the present invention, the organism signal measuring apparatus includes measuring means for effecting a measurement and an analysis of an organism signal of a subject for a predetermined period of time, input means for supplying said measuring means in advance with organism signal analysis data unique to an organism as a subject of the measurement, and display means for displaying results of the measurement and the analysis wherein said measuring means, after receiving the organism signal analysis data from said input means, effects a measurement of organism signals of the subject for a predetermined period of time and analyzes in a realtime fashion the measured organism signals based on the organism signal analysis data so as to memorize results of the analysis such that when the measurement for the predetermined period of time is completed, the memorized living body signals are delivered to said organism signal display means.

According to a feature of the present invention, the measuring means measures living body signals as a learning measurement for a predetermined period of time and analyzes the signals prior to a measurement on a subject so as to judge the normality and the abnormality and the input means beforehand supplies initial values of organism signal analysis data to be employed in the judgement to the measuring means such that the organism signals measured and analyzed by the measuring means and the results of the analysis are delivered to display means, said input means being capable of supplying the measuring means with correction values of the organism signal analysis data based on the judgement conducted by an inspector for the produced organism signals.

According to another feature of the present invention, the organism signal may be an electrocardiographic signal.

According to another feature of the present invention, the measuring means conducts a judgement on an organism signal or a living body signal depending on a feature value and the input means measures various kinds of feature values of normal and abnormal organism signals which are measured by the measuring means in a learning measurement and which are judged by the inspector so as to produce normal and abnormal histograms for each feature value, to respectively measure a degree of separation or isolation between the normality and the abnormality for the respective values, to select a feature value having the largest degree of separation for use in the judgement of the organism signals, and to determine a threshold value of each feature value based on the degree of separation thereof, thereby supplying the measuring means with the threshold values of the feature values.

According to still another feature of the present invention, the feature value may be an area of the QRS portion, a peak value thereof, or a value attained by dividing the area by the peak value.

According to another feature of the present invention, the measuring means measures organism signals by use of a template matching method and the input means generates a template for use in the template matching from the normal and abnormal organism signals which are measured by the measuring means in a learning measurement and which are judged by the inspector so as to set threshold values of correlation coefficients for the judgement of the template matching based on the organism signals, thereby supplying the measuring means with the template and the threshold values of the correlation coefficients.

According to another feature of the present invention, the correlation coefficients CORRi are represented with a QRS waveform $\vec{F}$ and a template $\vec{Ti}$ as follows.

$$CORRi = \vec{Ti} \cdot \vec{F} / |\vec{Ti}| |\vec{F}|$$

The measuring means may employ as a condition to judge a presence of a correlation between the QRS waveform $\vec{F}$ and the template $\vec{Ti}$ a fact that there exists the following relationship between the correlation coefficients CORRi and the threshold value TCR thereof.

$$CORRi > TCR$$

According to another feature of the present invention, the measuring means may employ as a condition to judge a presence of a correlation between the QRS waveform $\vec{F}$ and the template $\vec{Ti}$ a fact that there exists the following relationship between a ratio DNORM of a difference of norms attained from DNORM- ABS($|\vec{F}|-|\vec{T}|$)/$|\vec{T}|$ and a threshold value TN of the ratio DNORM.

DNORM<TN

According to another feature of the present invention, the measuring means may employ as a renewed template for the template matching, the template $\vec{T}in$ being obtained by use of the old template $\vec{T}io$, the QRS waveform $\vec{F}$, and a renewal rate UR of the template from the following formula.

$$\vec{T}in = (1-UR)\vec{T}io + UR \cdot \vec{F}$$

According to another feature of the present invention, the measuring means can detect the QRS when the absolute value of a differential signal of an electro-cardiographic signal supplied thereto exceeds a predetermined threshold value.

In addition, according to the present invention, in an organism signal measuring apparatus which measures and analyzes organism signals of a subject for a predetermined period of time so as to produce analyzed data, by supplying the apparatus with organism signal analysis data, the characteristics of organism signals of the subject is learned by the apparatus.

According to another feature of the present invention, the organism signal measuring apparatus includes measuring means for measuring signals from an organism or a living body for a predetermined period of time, analyzing means for analyzing organism signals measured by the measuring means, storing means for storing a result of the analysis conducted by the analyzing means, and output means for outputting to an external device data stored in the storing means after the measurement and the analysis are completed wherein organism signals of a subject measured by the measuring means prior to a measurement is outputted from the output means and organism signal analysis data can be beforehand stored, the data including characteristics of organism signals of the subject set based on a judgement effected by an inspector on the organism signals.

According to another feature of the present invention, prior to a measurement, the analyzing means is beforehand loaded with initial values of organism signal analysis data such that the measuring means measures organism signals for a predetermined period of time as a learning measurement, that the analyzing means analyzes the organism signals so as to judge to determine the normality and the abnormality, that a result of the judgement is outputted from the output means, and that correction values of the organism signal analysis data based on the judgement of the inspector effected on the outputted organism signals are supplied to the analyzing means.

According to another feature of the present invention, the organism signal may be an electrocardiographic signal.

According to another feature of the present invention, the analyzing means judges the organism signals, feature values or characteristic quantities to be adopted in the judgement are measured by the measuring means in the learning measurement, various kinds of feature values are measured for organism signals judged by the inspector to be respectively normal and abnormal, histograms of the normal and abnormal organism signals are produced for each feature value, a degree of separation between the normality and the abnormality is measured for the histogram, a feature value having the greatest degree of separation is selected for the judgement of the organism signals, a threshold value of the feature values is determined according to the degree of separation of the feature values, and the threshold value of the feature values is supplied to the analyzing means.

According to another feature of the present invention, the feature values may be an area of the QRS portion, the peak value thereof, or a value obtained by dividing the area by the peak value.

According to another feature of the present invention, the analyzing means judges organism signals by use of a template matching method and there is generated a template for use in the template matching from the normal and abnormal organism signals which are measured by the measuring means in a learning measurement and which are judged by the inspector so as to set threshold values of correlation coefficients for the judgement of the template matching based on the organism signals, thereby supplying the analyzing means with the template and the threshold values of the correlation coefficients.

According to another feature of the present invention, the correlation coefficients CORRi are represented with a QRS waveform $\vec{F}$ and a template $\vec{T}i$ as follows.

$$CORRi = \vec{T}i \cdot \vec{F} / |\vec{T}i||\vec{F}|$$

The analyzing means may employ as a condition to judge a presence of a correlation between the QRS waveform $\vec{F}$ and the template $\vec{T}i$ a fact that there exists the following relationship between the correlation coefficients CORRi and the threshold value TCR thereof.

CORRi>TCR

According to another feature of the present invention, the analyzing means may further employ as a condition to judge a presence of a correlation between the QRS waveform $\vec{F}$ and the template $\vec{T}i$ a fact that there exists the following relationship between a ration DNORM of a difference of norms attained from DNORM=ABS($|\vec{F}|-|\vec{T}1|$)/$|\vec{T}|$ and a threshold value TN of the ratio DNORM.

DNORM<TN

According to another feature of the present invention, the analyzing means may employ as a renewed template for the template maching, the template $\vec{T}in$ being obtained by use of the old template $\vec{T}io$, the QRS waveform $\vec{F}$, and an renewal rate UR of the template from the following formula.

$$\vec{T}in = (1-UR)\vec{T}io + UR \cdot \vec{F}$$

According to another feature of the present invention, the analyzing means can detect the QRS when the absolute value of a differential signal of an electro-cardiographic signal supplied thereto exceeds a predetermined threshold value.

BRIEF DESCRIPTION OF DRAWINGS

FIGS. 2a-2b are functional block diagrams showing an embodiment in which the present invention is applied to an electrocardiogram measuring apparatus;

FIG. 12 is a diagram showing an example of an analysis result displayed in a display unit in the apparatus of FIG. 2;

FIG. 13a is a graph showing an example of an electrocardiographic waveform;

FIG. 13b is a graph showing signals attained by differentiating the waveform of FIG. 13a;

FIG. 13c is a graph showing signals associated with absolute values of the signals of FIG. 13b;

FIG. 14 is a graph showing an area of the QRS portion;

FIG. 15 is a graph showing the amplitude of the QRS portion;

FIGS. 27a-27e are graphs showing examples of record attained as a result of a long-term electrocardiogram measurement by means of the apparatus of FIG. 2;

DESCRIPTION OF THE PREFERRED EMBODIMENTS

Referring next to the accompanying drawings, description will be given in detail of an embodiment in which the present invention is applied to a long-term electrocardiogram measuring apparatus.

Figure 4:
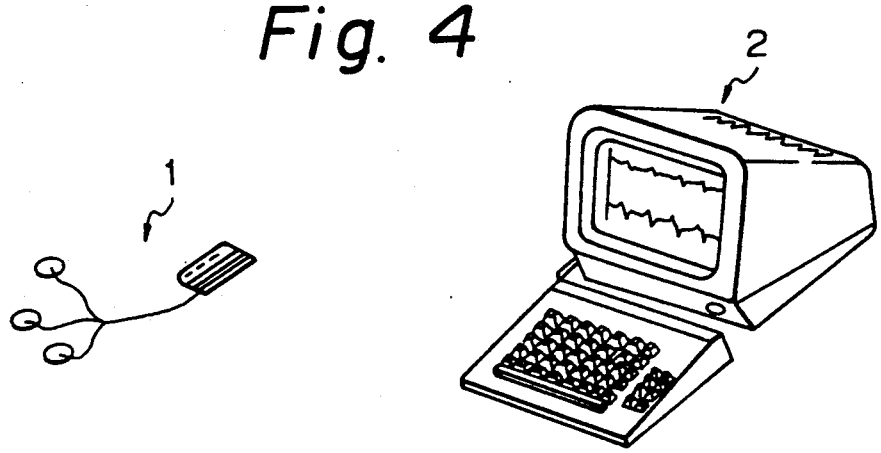
FIG. 4 is a diagram showing an outline of the apparatus of FIG. 2.

The long-term electrocardiogram measuring apparatus includes as shown in FIG. 4 a portable electrocardiographic apparatus (realtime analyzer) 1 to be attached to a portion of the body of a subject and a report generator 2 to be connected to the realtime analyzer 1.

Figure 5:
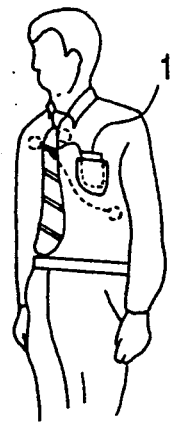
FIG. 5 is a diagram showing a state in which a long-term measurement of the electrocardiogram is effected by use of the apparatus of FIG. 2.

The realtime analyzer 1 may be carried about by the subject as shown in FIG. 5 such that electrocardiographic waveforms of the subject are measured for a long period of time, for example, 24 hours and that respective portions of the measured waveforms are judged for the determintion of the normality and abnormality thereof so as to memorize, for example, the portions of the waveforms judged to be abnormal.

The report generator 2 is connected, after the realtime analyzer 1 has completed a long-term measurement, to the realtime analyzer 1 so as to output the judged result therefrom for a confirmation to be conducted by an inspector, for example, a doctor.

Figure 6:
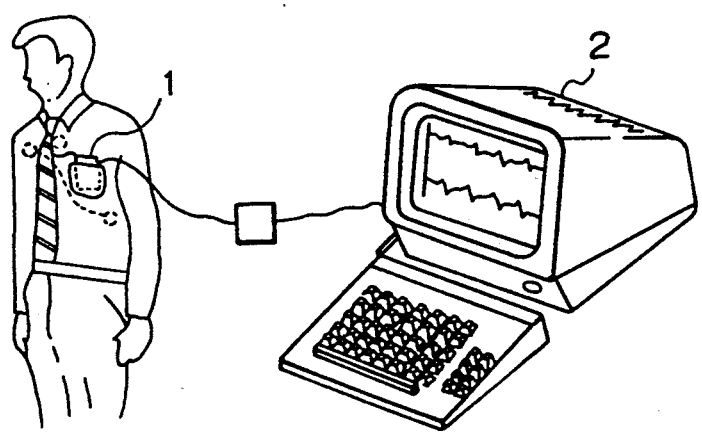
FIG. 6 is a diagram showing a state at the learning operation prior to the operation in which a long-term measurement of the electrocardiogram is effected by use of the apparatus of FIG. 2.

In addition, the report generator 2 is also employed, before the realtime analyzer 1 is attached to the subject for the long-term measurement, as shown in FIG. 6 so as to supply judgement standards or reference values for the judgement to the realtime analyzer 1 or to correct the reference values stored in the realtime analyzer 1.

The operations to supply and to correct the reference values for the judgement are accomplished such that after the realtime analyzer 1 is attached to the subject and a certain amount of electrocardiographic data items are gathered, the realtime analyzer 1 is supplied with reference values for the judgement or such that the general reference values for the judgement beforehand stored therein are directly corrected.

Figure 1:
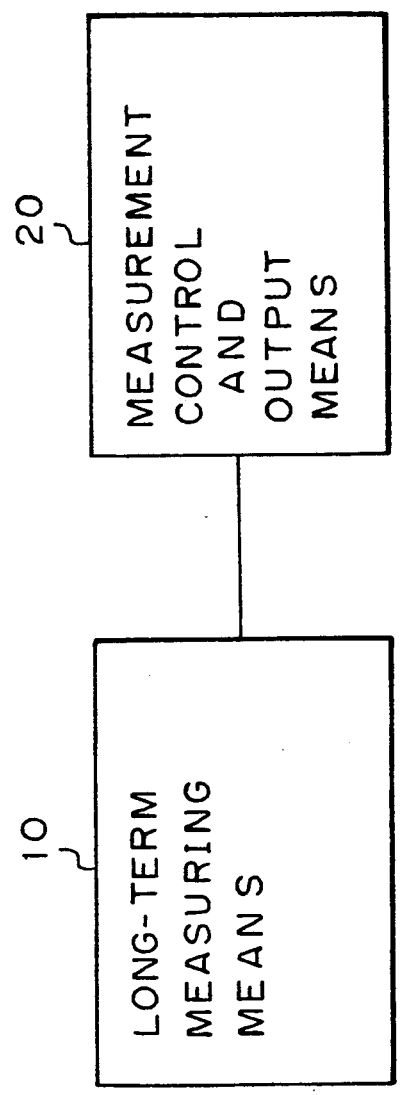
FIG. 1 is a functional block diagram showing a constitution according to the present invention.
Figure 2A:
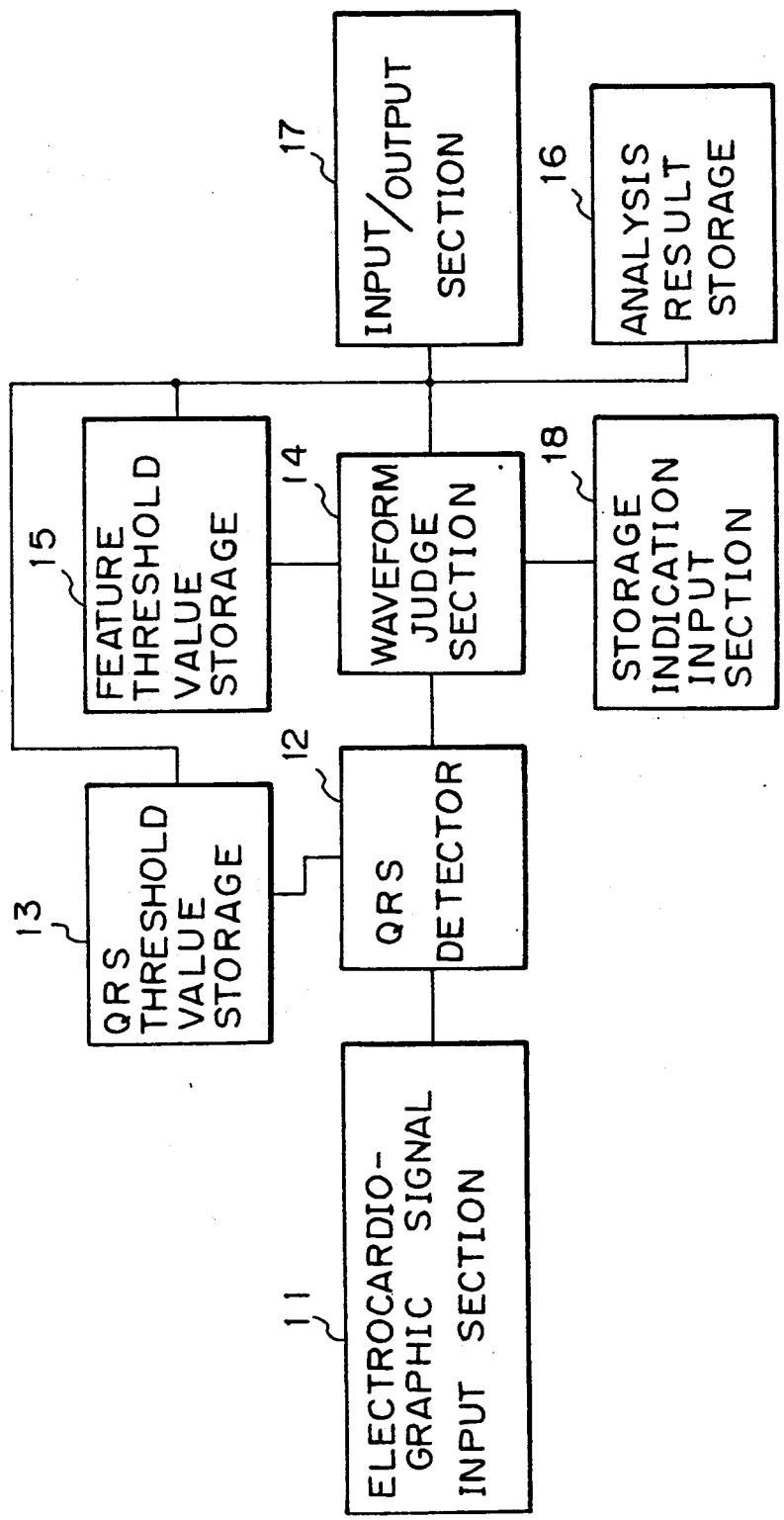

FIGS. 2a-2b are functional block diagrams showing a long-term electrocardiogram measuring apparatus as an embodiment according to the present invention in which electrocardiographic waveforms are judged by use of feature value thereof, wherein FIGS. 2a and 2b show portions of the realtime analyzer 1 and the report generator 2, respectivley.

In FIG. 2a, an electrocardiographic signal input section 11 receives as an input thereto an electrocardiograhic signal from a subject. A QRS detector 12 detects a QRS portion of the electrocardiographic signal received from the electrocardiographic signal input section 11 according to a method, which will be described hereafter. A QRS threshold value storage 13 stores therein a QRS threshold value TQRS employed for a detection of the QRS portion in the QRS detector 12.

A waveform judge section 14 judges the normality and the abnormality of the waveforms of the electrocardiographic signals in which a QRS portion is detected according to a method, which will be described later. A feature threshold value storage 15 stores therein threshold values of feature values adopted for the judgement of the waveforms in the waveform judge section 14.

An analysis result storage 16 stores therein a result of the judgement conducted on the waveforms in the waveform judge section 14 and the waveforms judged to be abnormal. An input/output section 17 is connected to an input/output section 21 of the report generator 2 of FIG. 2b so as to communicate data therebetween. For example, the analysis results of the long-term measurement stored in the analysis result storage 16 are read out so as to be delivered to the report generator 2, or the QRS threshold value TQRS and threshold vaues of respective feature value are inputted from the report generator 2 so as to be supplied to the QRS threshold value storage 13 and the feature threshold value storage 15.

A storage indication input section 18 is adopted to input a signal indicating storage of an electrocardiographic signal attained when the subject recognizes an abnormality of the heart during a long-term measurement effected with the realtime analyzer 1 attached to the body of the subject. When this signal is present, the electrocardiographic signal obtained at the pertinent moment is stored in the analysis result storage 16.

In FIG. 2b, the input/output section 21 is connected to the input/output section 17 of the realtime analyzer 1 so as to achieve data input/output operations with the realtime analyzer 1. A display 22 is used to display electrocardiographic signals and analysis results sent from the realtime analyzer 1 via the input/output section 21 and a signal processor 24.

An operation input section 23 is employed by an inspector to visually check the judgement result obtained from the realtime analyzer 1 and displayed on the display 22 so as to input a correction to be conducted on the judgement. In addition, the inspector inputs from the operation input section 23 various threshold values in advance when required.

The signal processor 23 corrects the judgement on the electrocardiographic signals in a case where an input for a correction of the judgement result conducted by the realtime analyzer 1 is supplied from the operation input section 24, which will be described later. A QRS threshold value correction or setting section 25 sets, based on the judgement corrected by the signal processor 24, a new threshold value TQRS for the detecton of the QRS portion and delivers the value TQRS via the input/output section 21 threshold value storage 13 of the realtime analyzer 1.

A feature value measuring section 26 measures feature values of electrocardiographic waveforms attained by correcting the judgement received from the signal processor 24. A feature value histogram generator 27 produces a histogram of the respective feature value measured by the feature value measuring section 26, which will be described later. A feature value selector 28 selects, based on the histogram of the feature values created by the feature value histogram generator 27, one of the feature values for the judgement of the waveforms.

A feature threshold value setting section 29 determines a threshold value for the judgement of the feature values selected by the feature value selector 28 according to a method, which will be described later, so as to supply the threshold values via the input/output section 21 to the feature threshold value storage 15 of the realtime analyzer 1.

Figure 7:
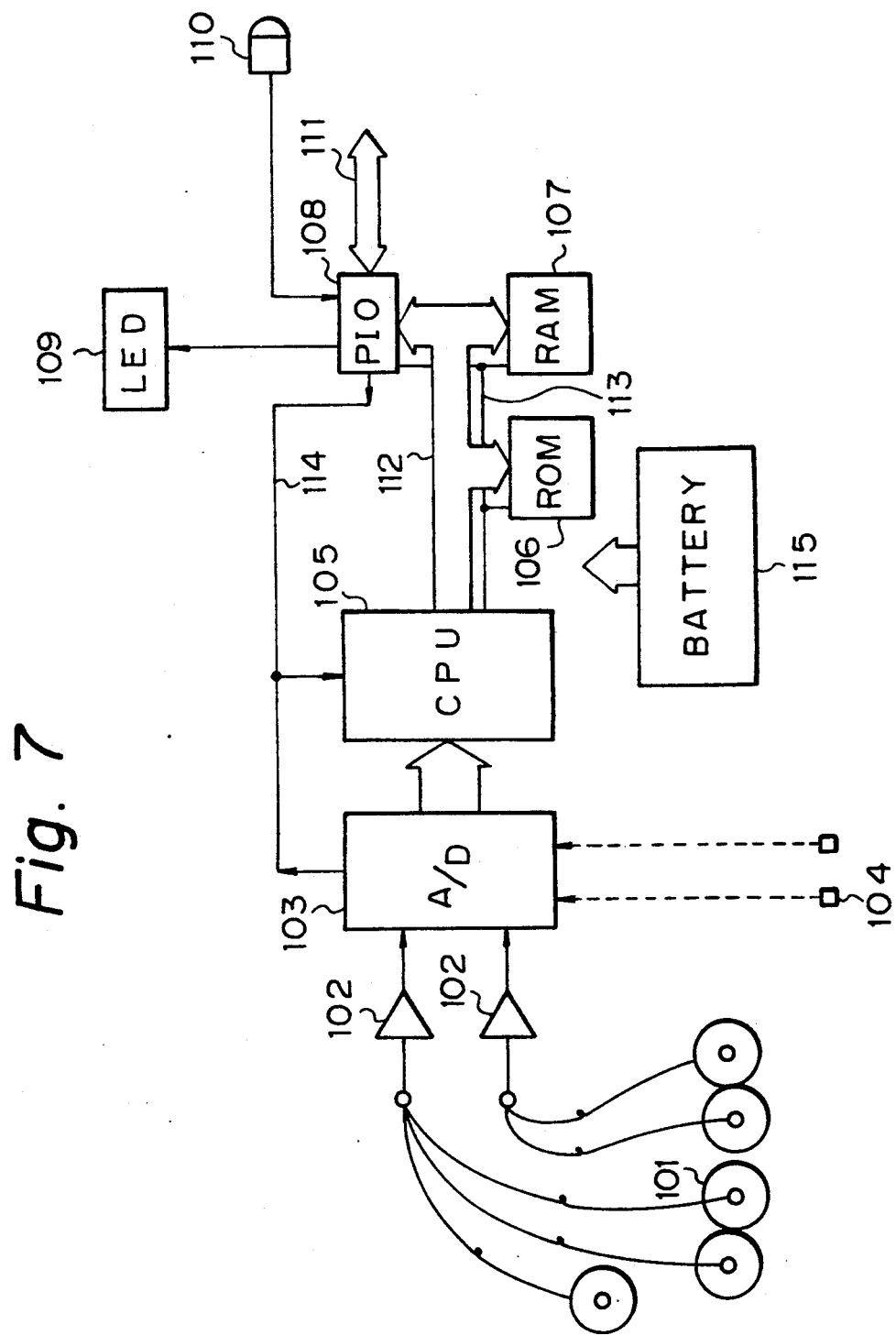
FIG. 7 is a block diagram showing a hardware configuration of a realtime analyzer of FIG. 2.

FIG. 7 shows a block diagram of a hardware constitution of the realtime analyzer 1.

As shown in FIG. 7, the realtime analyzer 1 has a plurality of electrodes 101 for the electrocardiogram. In a measurement, as well known, the electrodes 101 are brought into contact with predetermined portions of the body of the subject so as to collect electrocardiographic signals of the subject. The electrodes 101 are oridinarily of a disposal type.

An induction method to produce an electrocardiogram, namely, locations where the electrodes 101 are mounted are selected depending on purposes in a case of a single induction, as well known, according to (1) NASA induction, (2) CM5 induction, or (3) CC5 induction.

In a case of the double induction, the locations are selected depending on a combination of (1) and (2) or (1) and (3). Incidentally, in either case of the single and double inductions, grounding electrodes are naturally necessary.

A differential amplifier 102 for the electrocardiogram is connected to the plural electrodes 101 so as to amplify electrocardiographic signals received therefrom. An analog-to-digital, AD converter 103 is supplied with the signals amplified by the differential amplifier 102 and a signal supplied from an auxiliary input terminal 104 for inputting other organism information when required such that these signals are converted from analog values into digital values to be supplied to a central processing unit, CPU 5. The electrodes 101, the differential amplifier 102, the AD converter 103, and the auxiliary input terminal 104 constitute the electrocardiographic signal input section 11 of FIG. 2a.

The CPU 105 analyzes the electrocardiographic signals inputted from the AD converter 103 by use of a control program and an analysis program for analyzing the signals stored in a read only memory, ROM 106 and a random access memory, RAM 107 so as to store a result of the analysis together with the raw data of the signals in the RAM 107.

The ROM 106 is disposed to store therein a program to control the CPU 105 and a program to analyze the electrocardiographic signals in a realtime fashion. The RAM 107 is loaded with a program to analyze the signals, electrocardiographic signal data inputted from the electrodes 101 and undergone the AD conversion in the AD converter 103, and data attained as a result of an analysis conducted by the analysis program on the electrocardiographic signal data. The CPU 105, the ROM 106, and the RAM 107 constitute the QRS detector 12, the QRS threshold value storage 13, the waveform judge section 14, the feature threshold value storage 15, and the analysis result storage 16.

The input/output section 17 of FIG. 2a includes a parallel input/output, IO 108 and an output data and control bus 111.

The parallel IO 108 is a parallel input/output device and is connected to an address data bus 112, a control bus 113, and an interrupt signal bus 114 such that input/output operations thereof are controlled by the CPU 105 so as to generate an interrupt signal via the interrupt signal bus 114 onto the CPU 105 depending on an external state. An LED 109 is connected to an output port of the parallel IO 108 so as to display an operation state of the realtime analyzer 1. In addition, the LED 109 also notifies the subject the condition that the report generator 2 is in an operative state.

An event marker switch 110 constitutes the storage indication input section 18 of FIG. 2a and is connected to an input port of the parallel IO 108 such that the switch 110 is depressed when the subject recognizes an abnormality of the heart so as to generate an interrupt signal onto the interrupt signal bus 114. In response to the interrupt signal, the CPU 105 instructs the RAM 107 to store an electrocardiographic waveform developed at the moment. The output data and control bus 111 is connected to an input/output terminal of the parallel IO 108 so as to communicate instructions and data between the realtime analyzer 1 and the report generator 2.

A battery 115 is the primar power source of the realtime analyzer 1 and has a capacity required for the realtime analyzer 1 to effect the measurement and the analysis of the electrocardiographic signals for 24 hours or a longer period of time.

Figure 8:
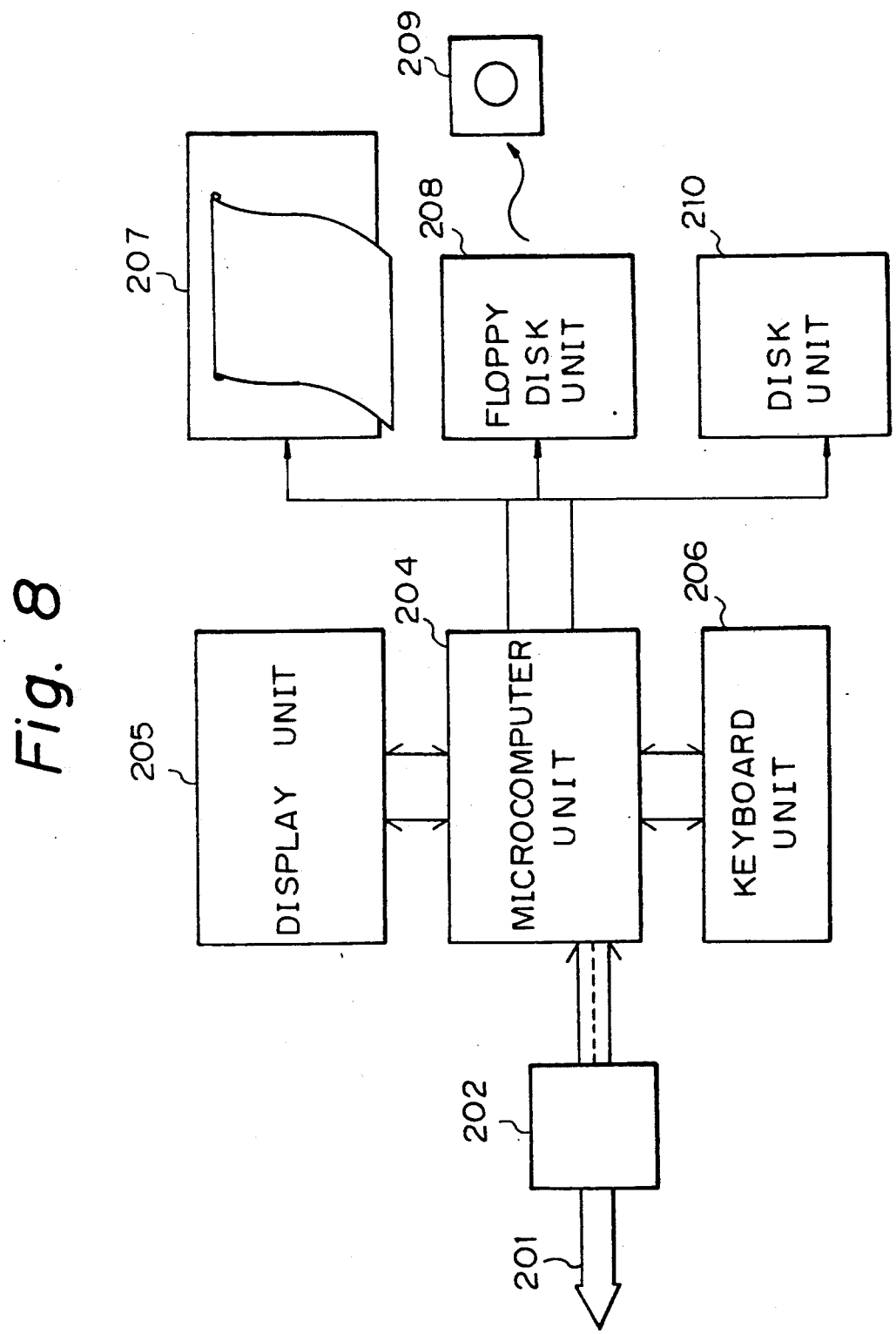
FIG. 8 is a block diagram showing a hardware configuration of a report generator of FIG. 2.

FIG. 8 shows a block diagram of the hardware consititution of the report generator 2.

The report generator 2 displays the waveforms and results attained through a realtime analysis by the realtime analyzer 1. In addition, the report generator 2 displays the results of the measurement and analysis of the subject beforehand effected by the realtime analyzer 1 prior to a long-term electrocardiogram measurement, so that an inspector corrects the analysis results thus displayed, which causes a learning operation to be achieved so as to correct the analysis program stored in the RAM 107 of the realtime analyzer 1 according to the results of the learning operation.

As shown in FIG. 8, the report generator 2 includes an isolation unit 202. Which is connected via a communication line 201 to the output data and control bus 111 of the realtime analyzer 1 so as to establish an electric connection between the realtime analyzer 1 and the report generator 2 for the following operation. That is, as described above, before a long-term electrocardiogram measurement, the realtime analyzer 1 is attached to the body of the subject such that the realtime analyzer 1 is connected to the report generator 2, which then confirms the electrocardiogram mesurement and learns the personal characteristics of the subject. The isolation unit 202 and the communication line 201 constitute the input/output section of FIG. 2b.

The isolation unit 202 is connected to a microcomputer unit 204, which is supplied via the isolation unit 202 data and the analysis result of the cardiographic waveforms meansured by the realtime analyzer 1. The microcomputer unit 204 is connected to a display unit 205, which displays the measurement data and the analysis result from the microcomputer unit 204. A keyboard unit 206 is linked to the microcomputer unit 204 so as to converse with the inspector. The display unit 205 and the keyboard unit 206 respectively constitute the display section 22 and the operation input section 23, whereas the microcomputer unit 204 comprises the signal processor 24, the QRS threshold value setting section 25, the feature value measuring section 26, the feature value histogram generator 27, the feature value selector 28, and the feature threshold value setting section 29.

The inspector, for example, a doctor confirms an electrocardiographic waveform and the judgement on the normality or the abnormality of the waveform displayed on the display unit 205 and then inputs, for a wrong judgement, a notification thereof from the keyboard unit 206. In addition, the keyboard unit 206 is used to input indications for outputting the measurement result or thee analysis result to a printer 207, a floppy disk 208, or a hard disk unit 210.

Next, referring to the flowchart of FIG. 9, an operation of the apparatus of this embodiment will be described.

First, in step 1000, the realtime analyzer 1 is attached to the body of the subject. After determining the induction method, the electrocardiographic electrodes are fixed on predetermined portions of the body. The main body of the realtime analyzer 1 is brought about by the subject.

In step 2000, the realtime analyzer 1 is connected to the report generator 2 as shown in FIG. 6.

In step 3000, an electrocardiographic, ECG waveform is measured so as to be displayed on the display unit 205 of the report generator 2, thereby confirming whether or not the measurement is appropriately achieved.

When the realtime analyzer 1 is connected to the report generator 2, an ECG signal of the subject supplied from the electrode 101 is delivered to the differential amplifier 102, which in turn amplifies the received signal so as to feed the amplified result to the AD converter 103. In addition, if necessary, a signal supplied from the auxiliary input terminal 104 is also inputted to the AD converter 103.

These ECG signals are converted into digital signals through the AD converter 103 so as to be fed to the CPU 105, which then analyzes the ECG signals received from the AD converter 103 according to the control program and the analysis program stored in the ROM 106 and the RAM 107 in a method, which will be described later, so as to store a result of the analysis together with the ECG signals in the RAM 107. Incidentally, without using the CPU 105, this analysis may be accomplished by the microcomputer unit 204 of the report generator 2.

The ECG signal and the analysis result thereof are also supplied to the microcomputer unit 204 via the output data and control bus 111, the communication cable 201, and the isolation unit 202. After accomplishing necessary processing on these signals, the microcomputer unit 204 sends the resultant signal to the display unit 205, which then displays the measured ECG waveform and the analysis result thereof as shown in FIG. 12. In a case where the analysis of the ECG signals is conducted by the microcomputer unit 204, the ECG signals undergone the analysis are sent together with the analysis result thereof to the display unit 205 so as to be displayed thereon. For the analysis result, a triangular mark is indicatd at an R peak of the waveform and latters N and V are indicated for the normal and abnormal portions, respectively.

By visually checking the data displayed on the display unit 205, the inspector, for example, a doctor confirms that the ECG waveform is measured with a satisfactory stability.

Next, in step 4000, the inspector appropriately corrects the analysis result of the ECG waveform displayed on the display unit 205 and effects a learning operation of the personal characteristics of the subject on the realtime analyzer 1. That is, the analysis result of the ECG waveform displayed on the display unit 205 is judged according to the general judgement standards or reference values beforehand stored in the realtime analyzer 1 or the report generator 2 without taking the personal characteristices of the subject into consideration; in consequence, the judgement may be inappropriate in some cases. In such a case, the inappropriate judgement is corrected by the inspector through an input operation from the keyboard 206. The realtime analyzer 1 corrects the judgement standards based on the judgement result thus corrected by the inspector. In other words, the realtime analyzer 1 learns the personal characteristics of the subject.

As will be described later, the realtime analyzer 1 in which the judgement standards have been corrected is carried about by the subject so as to conduct a long-term ECG measurement and to analyze measured ECG signals in a realtime fashion such that, for example, only the portions of ECG waveforms judged to be abnormal as a result of the analysis are stored therein.

Incidentally, it may also possible, without beforehand setting the judgement standards of the ECG signals to the realtime analyzer 1 or the report generator 2, that the ECG signals measured in the step 3000 are directly displayed on the display unit 205, so that the inspector visually checks the displayed ECG waveform to judge the normality or the abnormality thereof. In this case, the judgement standards are set for the first time by the judgement of the inspector so as to be stored in the realtime analyzer 1.

Figure 10:
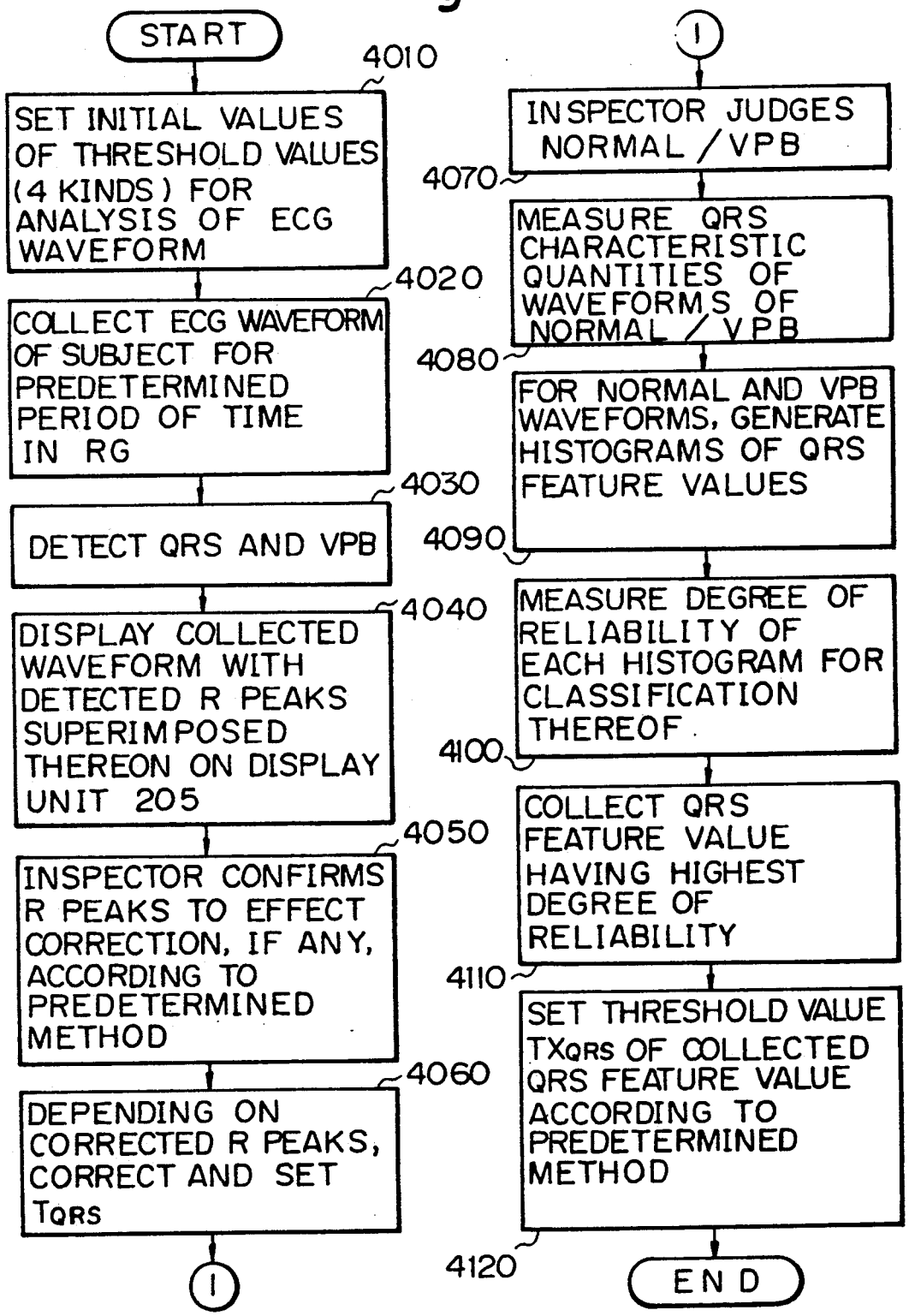
FIG. 10 is a flowchart showing an operation of the learning process of the apparatus of FIG. 2.

Referring here to the flowchart of FIG. 10, description will be given in detail of the learning process of the step 4000.

First, in step 4010, in order to conduct an analysis of the ECG waveform, the initial values of the four threshold values TAQRS, TAQRS, TTIQRS, and TQRS are set to the RAM 107 of the realtime analyzer 1.

Description will now be given of the threshold values TAQRS, TSQRS, TTIQRS, and TQRS.

A typical ECG waveform has a contour as shown in FIG. 13a, namely, such a waveform repeatedly appears at a cycle of one waveform per second. In consequence, in order to effect an automatic analysis of the arrhythmia, it is first necessary to detect the appearance of the QRS portion in the waveform as shown in FIG. 13a. In particular, the R peak is required to be correctly detected.

For the detection of the R peak, the ECG waveform of FIG. 13a is differentiated to obtain a waveform of FIG. 13b. As can be seen from FIGS. 13a-13b, a maximal value X1 and a minimal value X2 are respectively found before and after the R peak in the differentiated waveform. Absolute values DECG of the differentiated waveforms are represented in a graph of FIG. 13c. In order to detect a presence of the R peak, namely, the QRS portion based on the absolute values of FIG. 13c, there is sett a threshold value TQRS as shown therein. In a case of

DECG>TQRS the portion is regarded as the QRS as shown in FIG. 13c, thereby detecting the presence of the QRS portion. In consequence, the TQRS is feature value for the detection of the QRS portion.

When the QRS portion is detected, an operation is achieved to detect in this area a portion having a miximum value in the ECG waveform of FIG. 13a so as to judge the portion to be the R peak. The R peak is detected as described above.

Next, description will be given of three feature values or characteristic quantities employed to discriminate a normal waveform from an abnormal waveform (of the arrhythmia) in the QRS portion.

These feature values include an area AQRS of the QRS portion, an amplitude SQRS thereof, and a time index TIQRS thereof.

The area AQRS of the QRS portion represents, as indicated by the shade portion in FIG. 14, an area of the portions of the ECG waveform enclosed with the QRS portion and the base line, which is attained by integrating the absolute values of the ECG waveform in a predetermined time width, base line interval B—B', before and after the R peak. The points associated with the time width of the base line interval B—B' are set, for example, to 60 miliseconds before the R peak and to 120 milliseconds thereafter, respectively.

The amplitude SQRS of the QRS portion represents the height of the QRS portion of the ECG waveform, which is computed, as shown in FIG. 15, by attaining the maximum value M and the minimum value N of the ECG waveform in the base line interval B—B' so as to calculate value MN of the difference therebetween. The maximum and minimum values M and N respectively designate levels of the ECG waveform at the point R and S.

The time index TIQRS is an index of the width of the QRS portion of the ECG waveform, which is significant for the judgement of the arrhythmia. The time index TIQRS is obtained by dividing the area AQRS of the QRS portion by the amplitude SQRS thereof. That is, the time index TIQRS is defined as TIQRS=AQRS/SQRS. For the judgement of the normality or abnormality (arrhythmia) of each QRS portion of the ECG waveform, predetermineed threshold values are determined for either one of or all of these three feature values such that it is judged for each QRS portion of the measured ECG waveform to determine whether or not the feature values thereof exceed the associated threshold values.

For the threshold value TQRS to detect the presence the the QRS portion and the threshold values of the three feature values to judge he normality or the abnormality (arrhythmia) of each QRS portion as described above, the initial values are set in the step 4010 to the RAM 107 of the realtime analyzer 1.

In step 4020 subsequent thereto, the ECG waveform of the subject is measured for a predetermined period of time, for example, one minute to three minutes, or favorably, about five minutes so as to collect the measured waveform via the realtime analyzer 1 into the report generator 2.

In the next step 4030, the measured ECG waveforms are processed to detect therein R peaks of QRS portions and the arrhythmia. The detection of the R peak is judged, as described above, by determined in the QRS detector 12 whether or not the absolute value of the differentiated ECG waveform exceeds the threshold value TQRS read from the QRS threshold value storage 13 such that an R peak is judged to be present in a case of DECG>TQRS.

In addition, the detection of the arrhythmia is effected such that in the waveform judge section 14, the feature values AQRS, SQRS, and TIQRS are computed for each QRS portion of the mesured ECG waveform so as to be compared with the initialized values of the threshold values TAQRS, TSQRS, and TTIQRS stroed in the feature threshold value storage 15. the arrhythmia (VPB) is assumed when AQRS is greater than the threshold value TAQRS, when SQRS is higher than the threshold valve TSQRS, and TIQRS is widger than the threshold value TTIQRS. The normal waveform is assumed for other cases.

In step 4040, as shown in FIG. 12, the collected ECG waveform is displayed with the detected R peaks and indications of the arrhythmia (VPB) superimposed thereon on the display unit 205. In FIG. 12, the triangular mark denotes an R peak and letters N and V denote the normal waveform and the arrhythmia (VPB) waveform, respectively.

In step 4050, the iinspector visually checks the measured waveform displayed on the display unit 205 and the marks of the R peaks indicated therein so as to judge whether or not the marks are appropriately indicated.

Figure 16:
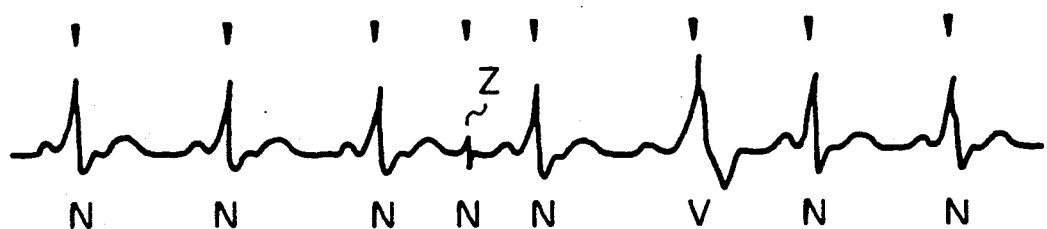
FIGS. 16-19 are graphs respectively showing examples of anaylsis results displayed on a display unit of the apparatus of FIG. 2.

For example, there may exist a case where a noise Z, as denoted in FIG. 16, is judged to be an R peak. This occurs because the initialized threshold value TQRS is set to a too small value. When such a portion is detected. the inspector indicates the portion by means of a device such as a light pen or a mouse and then depresses as an indication of a misjudgement, for example, the Error key on the keyboard unit 206.

Figure 17:
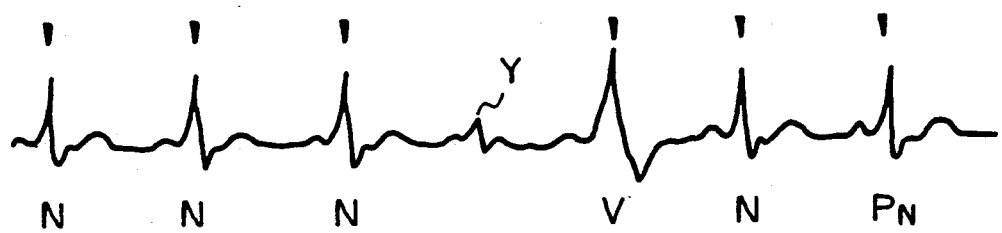

In addition, the detection of an R peak is unsuccessful in some cases like in a case of the portion Y in FIG. 17. This occurs due to a too great value initially set to the threshold value TQRS. When such a portion is detected, the inspector also indicates the portion by means of a device such as a light pen or a mouse and then depresses as an indication of an R peak, for example, the R key on the keyboard unit 206.

In step 4060, based on the result of the correction achieved by the job of the step 4050, the value of TQRS is set again. That is, the QRS threshold value setting section 25 sets the threshold value TQRS to an R peak having the minimum absolute values X1 and X2 in the differentiated, waveform, the R peak being selected from those having undergone the correction in response to an indication made by means of a device such as a light pen or a mouse, thereby sending the threshold value TQRS via the input/output section 21 to the realtime analyzer 1. As a result, the threshold value TQRS for the detection of the R peak set by use of a general value and stored in the QRS threshold value storage 13 is corrected to be the threshold value TQRS obtained by taking the personal characteristics in consideration.

In the subsequent step 4070, the inspector visually checks the indications of the normality (N) and the abnormality (V) of the R peaks displayed on display unit 205 so as to confirm whether or not the indications are appropriately assigned thereto.

Figure 18:
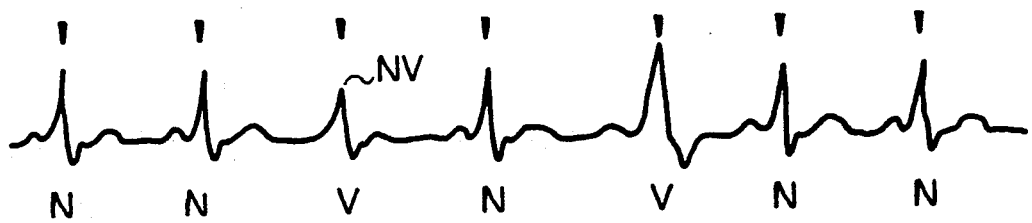

For example, in a case where there is found a portion NV in which a normal waveform is judged to be an arrhythmia VPB waveform as shown in FIG. 18, the inspector indicates the portion with a light pen or a mouse and then depresses as an indication of a normal waveform, for example, the Normal key on the keyboard unit 206.

Figure 19:
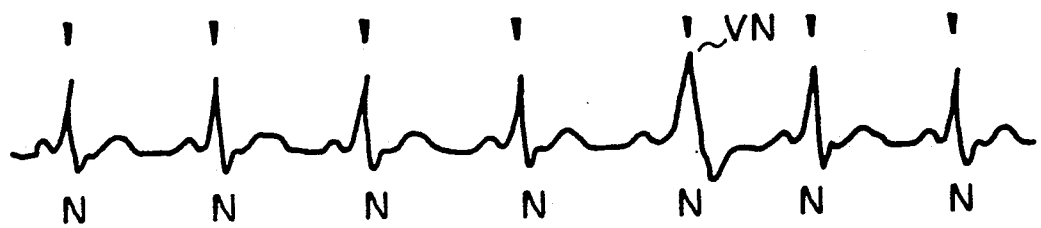

In addition, also in a case of a portion VN of FIG. 19 where an arrhythmia VPB waveform is judged to be noral N, the inspector indicates the portion with a light pen or a mouse and then depresses as an indication of an arrhythmia waveform, for example, the VPB key on the keyboard unit 206.

In step 4080, based on the result of the correction actieved by the job of the step 4070, the normal and arrhythmia (VPB) portions of the waveform are analyzed. That is, a learning operation of the personal characterisztics of the subject is effected by analyzing the respective normal and arrhythmia (VPB) portions of the waveform judged by the inspector.

The analysis of the waveform is accomplished in the feature value measuring section 26 by use of the QRS feature values AQRS, SQRS, and TIQRS for the respective normal and VPB portions of the waveform judged by the inspector. Namely, the are AQRS of the AQS portion is attained by integrating the absolute values of the ECG waveform in a predetermined time width (base line interval B—B') before and after the R peak, whereas the amplitude SQRS of the QRS portion is obtained by determining the maximum value M and the minimum value N of the ECG waveform in the base line interval B—B', thereby computing the absolute value of the difference M—N. The time index TIQRS of the QRS portion is attained by dividing the area AQRS of the QRS portion by the amplitude SQRS thereof.

Figure 20A:
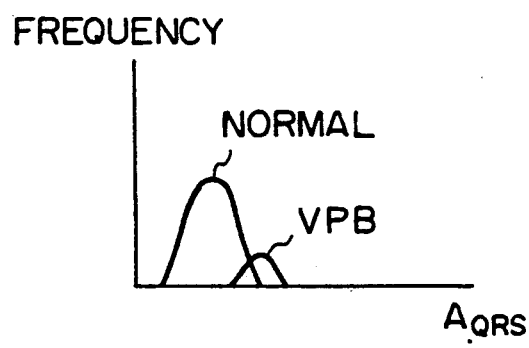
FIGS. 20a-20c are graphs respectively showing examples of histograms of AQRS, SQRS, and TIQRS.
Figure 20B:
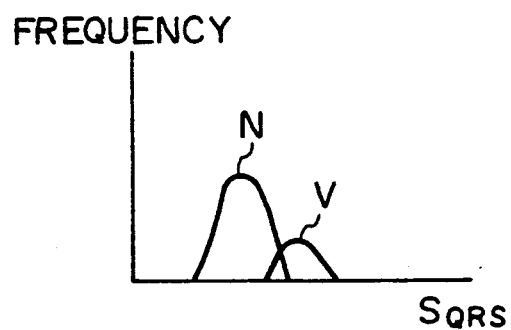
Figure 20C:
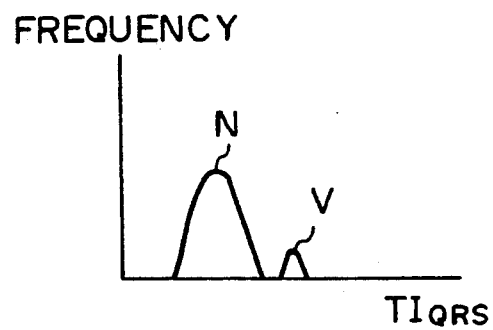

In step 4090, the feature values thus measured for the respective waveforms are processed in the feature value histogram generator 27 to respectively produce histograms for the normal waveform Normal and the abnormal waveform VPB. FIGS. 20a-20c respectively show examples of the created histograms.

FIG. 20a is a histogram of the values of the area AQRS of the QRS portion in which the normal waveform is distributed in a portion associated with the smaller AQRS values, whereas the abnormal VPB waveform is distributed in a portion associated with the greater AQRS values; furthermore, the normal and abnormal VPB waveforms are respectively distributed in a symmetric fashion along a vertical direction centered on the respective particular values. In this histogram, the AQRS values are overlapped for the normal and abnormal waveforms, and hence, for the AQRS values in this range, it is difficult to judge the normality or the abnormality. FIG. 20b is a histogram of the values of the amplitude SQRS of the QRS portion in which the normal waveform is distributed in a portion associated with the smaller SQRS values, whereas the abnormal VPB waveform is distributed in a portion associated with the greater SQRS values; furthermore, the normal and abnormal VPB waveforms are respectively distributed in a symmetric fashion in a vartical direction centered on the respective particular values. Also in this histogram, the SQRS values are overlapped for the normal and abnormal waveforms, and hence, for the SQRS values in this range, it is difficult to judge the normality or the abnormality.

FIG. 20c is a histogram of the values of the amplitude TIQRS of the QRS portion in which the normal waveform is distributed in a portion associated with the smaller TIQRS values, whereas the abnormal VPB waveform is distributed in a portion associated with the greater TIQRS values; furthermore, the normal and abnormal VPB waveforms are respectively distributed in a symmetric fashion in a vertical direction centered on the respective particular values. In this histogram, the TIQRS values are not overlapped for the normal and abnormal waveforms, namely, the respective TIQRS values are completely separated, and hence, for the SQRS values in this range, it is easy to judge the normality or the abnormality depending on the TIQRS values.

In step 4100, based on the histograms of the three feature values generated as described above, the degree of reliability is measured for each feature value for the classification thereof.

The degree of reliability is represented in five steps assigned as 0 to 4, which are defined as follows.

(1) Degree of reliability (ACC)=4

Figure 21:
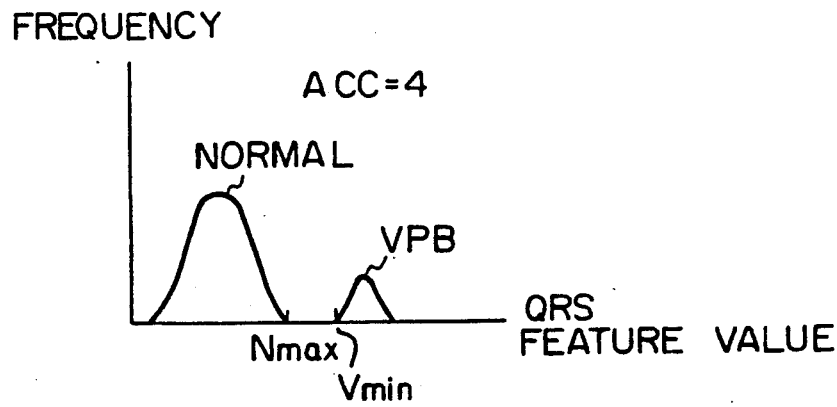
FIG. 21 is a graph showing an example of a histogram in a case where the degree of reliability of the feature value is four.

This corresponds to a case, as shown in FIG. 21, where in the histogram of the QRS feature value, the range of the feature values in which the normal waveform is distributed is completely separated from that of the feature values in which the abnormal VPB waveform is distributed, that is, a case where $$N_{max} < V_{min}$$

is satisfied, where Nmax is the maximum value of the feature values or characteristic quantity values in a population of the normal ECG waveforms, namely, the feature value of a waveform having the maximum feature value in the normal ECG waveforms. In addition, Vmin is the minimum value of the feature values in a population of the abnormal VPB ECG waveforms, namely, the feature value of a waveform having the minimum feature value in the abnormal VPB ECG waveforms. In a case where the inequality above is satisfied, the maximum value of the feature values in the normal ECG waveform population is smaller than the minimum value of the feature values in the abnormal VPB ECG waveform population, and the normal ECG waveform population is completely separated from the abnormal VPB waveform population as shown in FIG. 21. In consequence, in this case, the normal waveform and the VPB waveform can be separated from each other depending on the feature value, which results in a high degree of reliability.

Incidentally, for the greater difference between Nmax and Vmin, it is estimated that the discrimination capability between the normal and VPB waveforms is increased.

(2) Degree of reliability (ACC)=3

Figure 22:
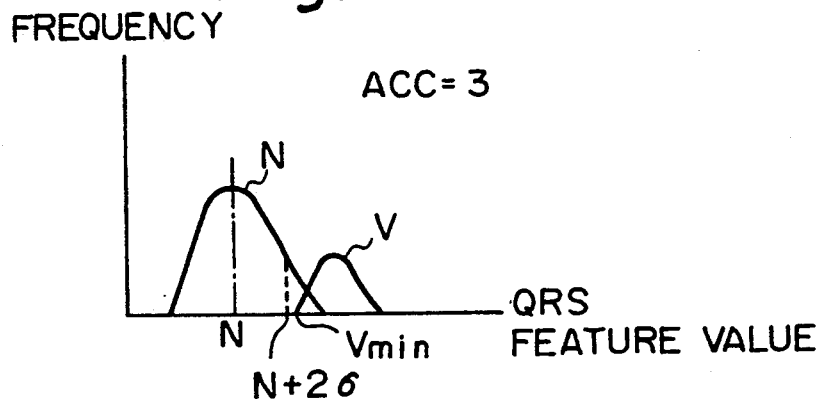
FIG. 22 is a graph showing an example of a histogram in a case where the degree of reliability of the feature value is three.

This corresponds to a case, as shown in FIG. 22, where in the histogram of the QRS feature value, the range of the feature values in which the normal waveform is distributed is slightly overlapped with that of the feature values in which the abnormal VPB waveform is distributed, that is, a case where $$N+2\sigma < V_{min} \leqq N_{max}$$

is satisfied, where N is the mean value of the feature values in a population of the normal ECG waveforms and $\sigma$ is the standard deviation of the feature value of the normal waveform population. In consequence, when this expression holds, the minimum value Vmin of the VPB ECG waveform population is not greater than the maximum value Nmax of the normal ECG waveform population, and hence these populations are partially overlapped with each other and the minimum value Vmin of the VPB ECG waveform population is greater than $N+2\sigma$, namely, only slight portions respectively thereof are overlapped with each other.

Assuming that the feature values of the normal ECG waveform form a normal distribution, 98% of the normal ECG waveform exists between $N+2\sigma$ and $N-2\sigma$. In consequence, the overlapped portion between the VPB and normal ECG waveform populations is less than 1% of the normal ECG waveform population. namely, the discrimination between the normal and VPB waveforms can be possible excepting this slight overlapped portion and hence the reliability of the judgement is considerably increased.

(3) Degree of reliability (ACC)=2

Figure 23:
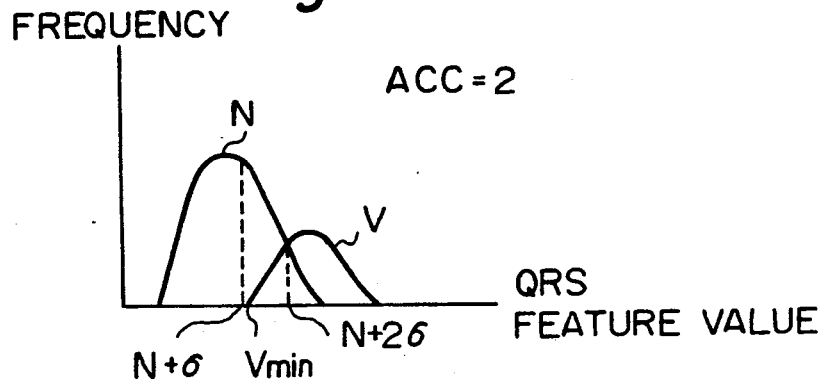
FIG. 23 is a graph showing an example of a histogram in a case where the degree of reliability of the feature value is two.

This corresponds to a case, as shown in FIG. 23, where in the histogram of the QRS feature value, as compared with the case of the degree of reliability=3, the range of the feature values in which the normal waveform is distributed is further overlapped with that of the feature values in which the abnormal VPB waveform is distributed, that is, a case where $$N+\sigma < V_{min} \leqq N+2\sigma$$

is satisfied.

When this expression holds, the minimum value Vmin of the VPB ECG waveform population is further smaller as compared with the case of the degree of reliability=3, and exists between $N+\sigma$ and $N=2\sigma$. In consequence, the greater portions are overlapped with each other, and hence the reliability of the judgement is decreased.

(4) Degree of reliability (ACC)=1

Figure 24:
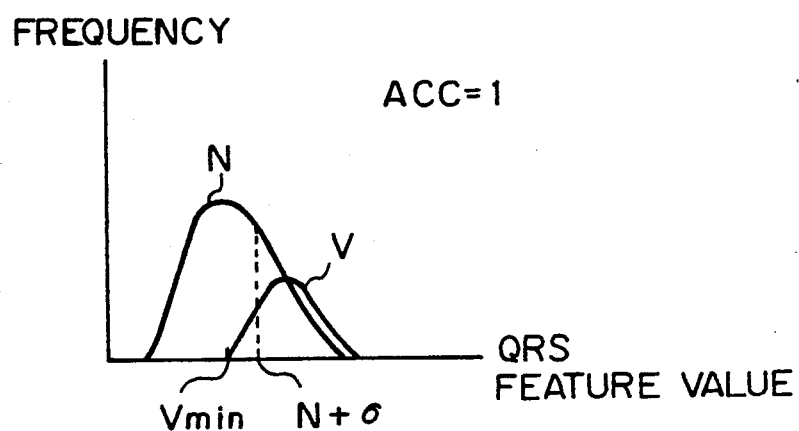
FIG. 24 is a graph showing an example of a histogram in a case where the degree of reliability of the feature value is one.

This corresponds to a case, as shown in FIG. 24, where in the histogram of the a QRS feature value, the range of the feature values in which the normal waveform is distributed is greatly overlapped with that of the feature values in which the abnormal VPB waveform is distributed, that is, a case where $$V_{min} \leqq N+\sigma$$

is satisfied.

When this expression holds, the minimum value Vmin of the VPB ECG waveform population is further smaller as compared with the case of the degree of reliability=3, and most portions of the VPB ECG waveform population overlap with the normal ECG waveform population. In consequence, the reliability of the judgement is considerably decreased.

(5) Degree of reliability (ACC)=0

Figure 25:
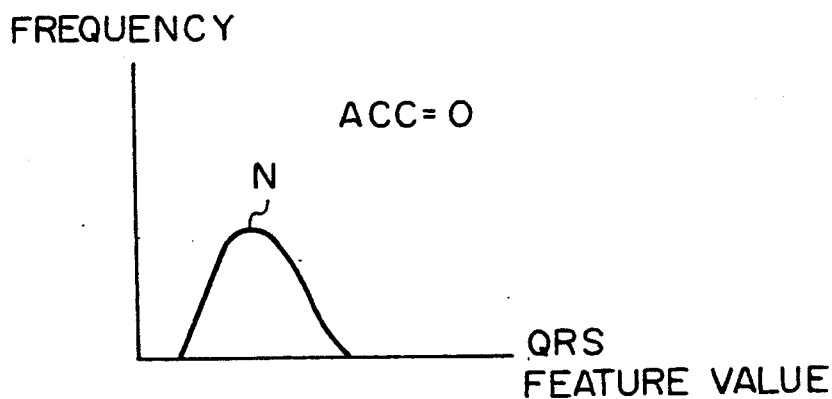
FIG. 25 is a graph showing an example of a histogram in a case where the degree of reliability of the feature value is zero.

In this case, as shown in FIG. 25, there exists only the normal ECG waveform population, namely, the abnormal VPB ECGG waveform population is absent.

That is, in this case, all ECG waveforms measured for the learning operation are normal and there does not appear any abnormal VPB ECG waveform. In this situation, only a distribution of the normal ECG waveform population can be measured and the feature values of the VPB ECG waveform population cannot be attained; in consequence, it is quite difficult to effect a discrimination between the normal and VPB waveforms.

As described above, the degree of reliability (ACC) of each feature value is determined according to the degree of the overlap between the normal ECG waveform population and the VPB ECG waveform population. In the judgement of the degree of reliability, since the normal waveforms are considered to be of a normal distribution, the mean value N and the standard deviation $\sigma$ are adopted for the judgement. However, the VPB waveforms are not necessarily associated with a normal distribution; furthermore, since there may exist a plurality of distribution populations, the mean value and the standard deviation of the VPB population are not employed for the judgement, namely, the maximum value Vmax and the minimum value Vmin are used therefore.

In the fashion as described above, the degrees of reliability are measured for the three QRS feature values AQRS, SQRS, and TIQRS. For example, in a case of the histograms of three QRS characteristic values AQRS, SQRS, and TIQRS shown in FIGS. 20a–20c, the degree of reliability (ACC) of the feature value TIQRS is 4 and the degrees of reliability of the feature values AQRS and SQRS are obtained as 3.

Next, in step 4110, there is determined a feature value having the highest degree of reliability among the three feature values so as to be used as the feature value for the analysis of the arrhythmia. This operation is accomplished in the feature value selector 28. That is, since the three feature values are assigned with the respective degrees of reliability in the step 4100, the judgement in the arrhythmia diagnosis is effected with priority levels assigned in the descending order of the degree of reliability. In the case of the three QRS feature values AQRS, SQRS, and TIQRS as shown in FIGS. 20a–20c, the feature value TIQRS assigned with the degree of reliability (ACC)=4 is adopted as the feature value for the arrhythmia analysis.

Incidentally, in a case where the respective feature values are of the same class, the difference with respect to the degrees of reliability is judged for the same class as follows.

First, when the feature values have the degree of reliability (ACC)=4, the feature value having the larger value of Vmin−Nmax is selected. That is, in this case, as shown in FIG. 21, since the normal ECG waveform population is completely separated from the VPB ECG waveform population without having an overlapped portion therebetween, the feature value having the greater degree of separation is selected. Since the minimum value Vmin of the feature values of the VPB ECG waveform population is greater than the maximum value Nmax of the feature values of the normal ECG waveform population, namely, Vmin>Nmax, the difference therebetween Vmin−Nmax is positive in any case, and hence the degree of separation is greater for the larger value of this difference, which indicates a high degree of reliability.

In a case where the feature values each have the degree of reliability (ACC)=3, the feature value having the larger value of Vmin−(N+2σ) is selected. That is, in this case, as shown in FIG. 22, the normal ECG waveform population is slightly overlapped with the VPB ECG waveform population such that the feature value having the smaller overlapped portion is selected. Since there is satisfied an inequality Vmin>N+2σ, Vmin−(N+2σ) is positive in any case, namely, for the larger value of this difference, there exists the smaller overlapped or duplicated portion, which indicates a higher degree of reliability.

In a case where the feature values each have the degree of reliability (ACC)=2, the feature value having the larger value of Vmin−(N+σ) is selected. That is, also in this case, as shown in FIG. 23, the normal ECG waveform population is overlapped with the VPB ECG waveform population such that the feature value having the smaller overlapped portion is selected. Since there is satisfied an inequality Vmin>N+σ, Vmin−(N+σ) is positive in any case, namely, for the larger value of this difference, there exists the smaller overlapped or duplicated portion, which indicates a higher degree of reliability.

In a case where the feature values each have the degree of reliability (ACC)=1, the feature value having the smaller value of (N+σ)−Vmin is selected. That is, in this case, as shown in FIG. 24, the normal ECG waveform population is overlapped with the VPB ECG waveform population such that the feature value having the smaller overlapped portion is selected. Since there is satisfied an inequality N+σ>Vmin, (N+σ)−Vmin is positive in any case, namely, for the larger value of this difference, there exists the smaller overlapped or duplicated portion, which indicates a higher degree of reliability.

In a case where the feature values each have the degree of reliability (ACC)=0, the feature values are selected in a priority order of TIQRS, AQRS, and SQRS. In this case, only the normal ECG waveform population appears in the measurement of the ECG waveforms, namely, the VPB ECG waveform population is not measured, in consequence, it is impossible to judge in which one of the histograms associated with the three feature values a satisfactory separation appears between the normal ECG waveform population and the VPB ECG waveform population.

Consequently, in this case, based on the histograms of the feature values of the measured ECG waveforms, it cannot be effected to judge which one of the three feature values is suitable for the discrimination between the normal ECG waveform population and the VPB ECG waveform. As described above, since the feature value suitable for the judgement cannot be selected depending on the individual characteristics of the subject, there is adopted in this case a procedure to select the feature value in the order above according to the general standards.

In general, the feature value suitable for the discrimination between the normal and VPB ECG waveforms is TIQRS, which is followed by AQRS and SQRS in this sequence.

After the QRS feature value having the highest degree of reliability is selected, step 4120 is executed to set a threshold value TXQRS selected and adopted as the QRS feature value to discriminate the normal and VPB ECG waveforms in a method, which will be described later. Incidentally, the TXQRS designates TAQRS, TSQRS, or TTIQRS when the selected QRS feature value is AQTS, SQTS, or TIQRS, respectively.

Figure 26:
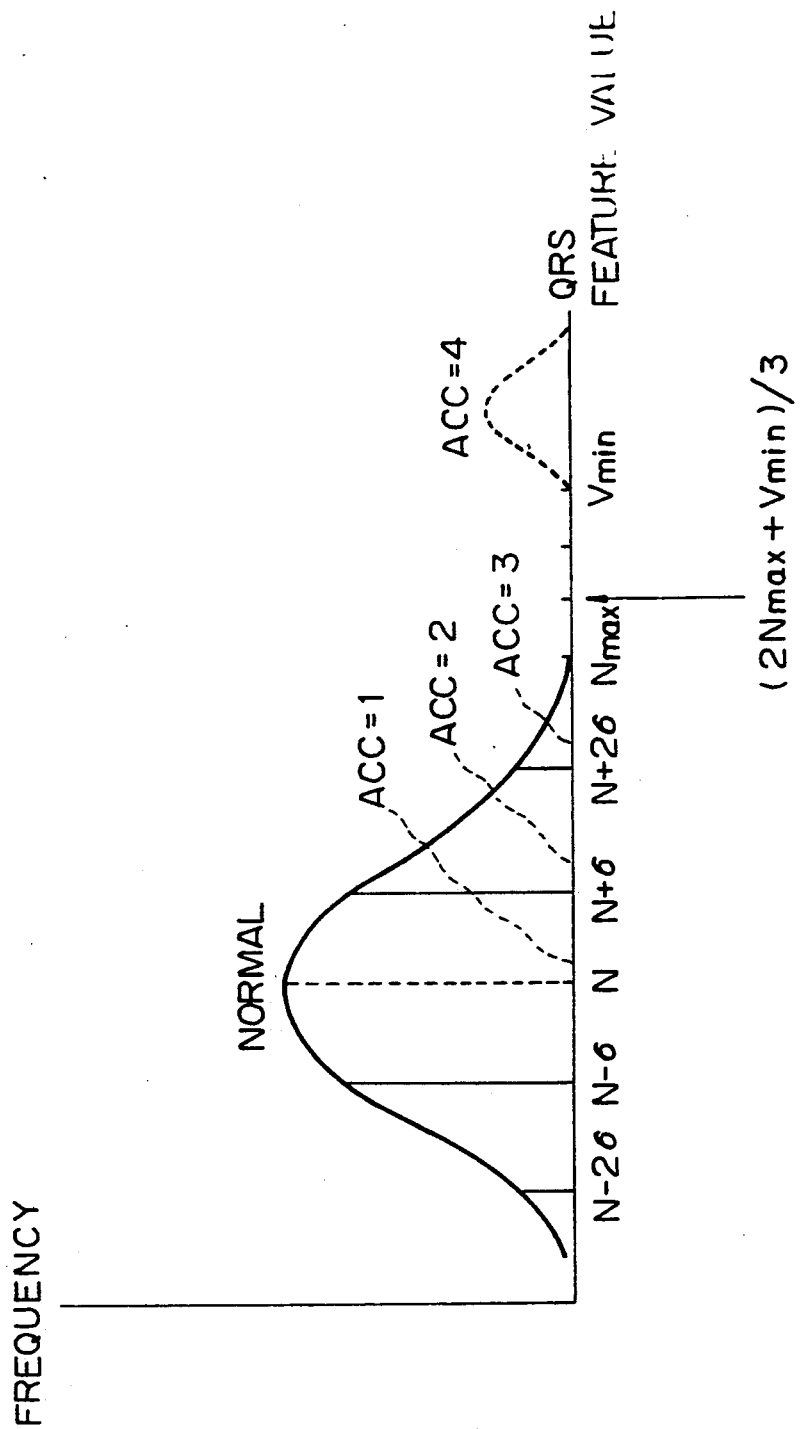
FIG. 26 is a graph showing a setting of a threshold value of the feature values.

The threshold value TXQRS is set, as shown in FIG. 26, for each degree of reliability as follows.

In a case of the degree of reliability=4, the following expression is employed.

$$TXQRS = (2Nmax + Vmin)/3$$

In this case, since the normal ECG waveform population is separated from the VPB ECG waveform population, the threshold value TXQRS is set between the maximum value Nmax of the normal ECG waveform population and the VPB ECG waveform population; furthermore, in order to minimize the chance to miss the VPB waveforms in the realtime analysis for 24 hours to be conducted later, the threshold value TXQRS is set to a position shifted from the intermediate point toward the maximum value Nmax.

In a case of the degree of reliability=3, the following expression is employed.

$$TXQRS = N + 2\sigma$$

In this case, since the normal ECG waveform population is overlapped with the VPB ECG waveform population, in order to minimize the chance to miss the VPB waveforms by judging the overlapped portion to be the VPB waveforms, the threshold value TXQRS is set to N+2σ.

In a case of the degree of reliability=2, the following expression is employed.

$$TXQRS = N + \sigma$$

In this case, like in the case of the degree of reliability=3, in order to minimize the chance to miss the VPB waveforms by judging the overlapped portion to be the VPB waveform, the threshold value TXQRS is set to $N+\sigma$.

In a case of the degree of reliability=1, the following expression is employed.

$$TXQRS = N+\sigma$$

In this case, like in the case above, in order to minimize the chance to miss the VPB waveforms, the threshold value TXQRS is to be set to N; however, in this situation, many normal ECG waveforms are judged to be VPB ECG waveforms and are hence missed in the judgement. Consequently, the threshold value TXQRS is set to $N+\sigma$.

In a case of the degree of reliability=0, the following expression is employed.

$$TXQRS = N+2\sigma$$

In this case, since the VPB ECG waveform population is not measured, the threshold value TXQRS is set to $N+2\sigma$ according to the general standards.

The operations to set these threshold values are accomplished in the characteristic quantity threshold value setting section 29.

Through the process of the step 4000, by taking the personal characteristics of the ECG waveforms of the subject into consideration, the suitable feature values are selected for the judgement of the normal and VPB ECG waveforms and the threshold values thereof are determined.

Figure 9:
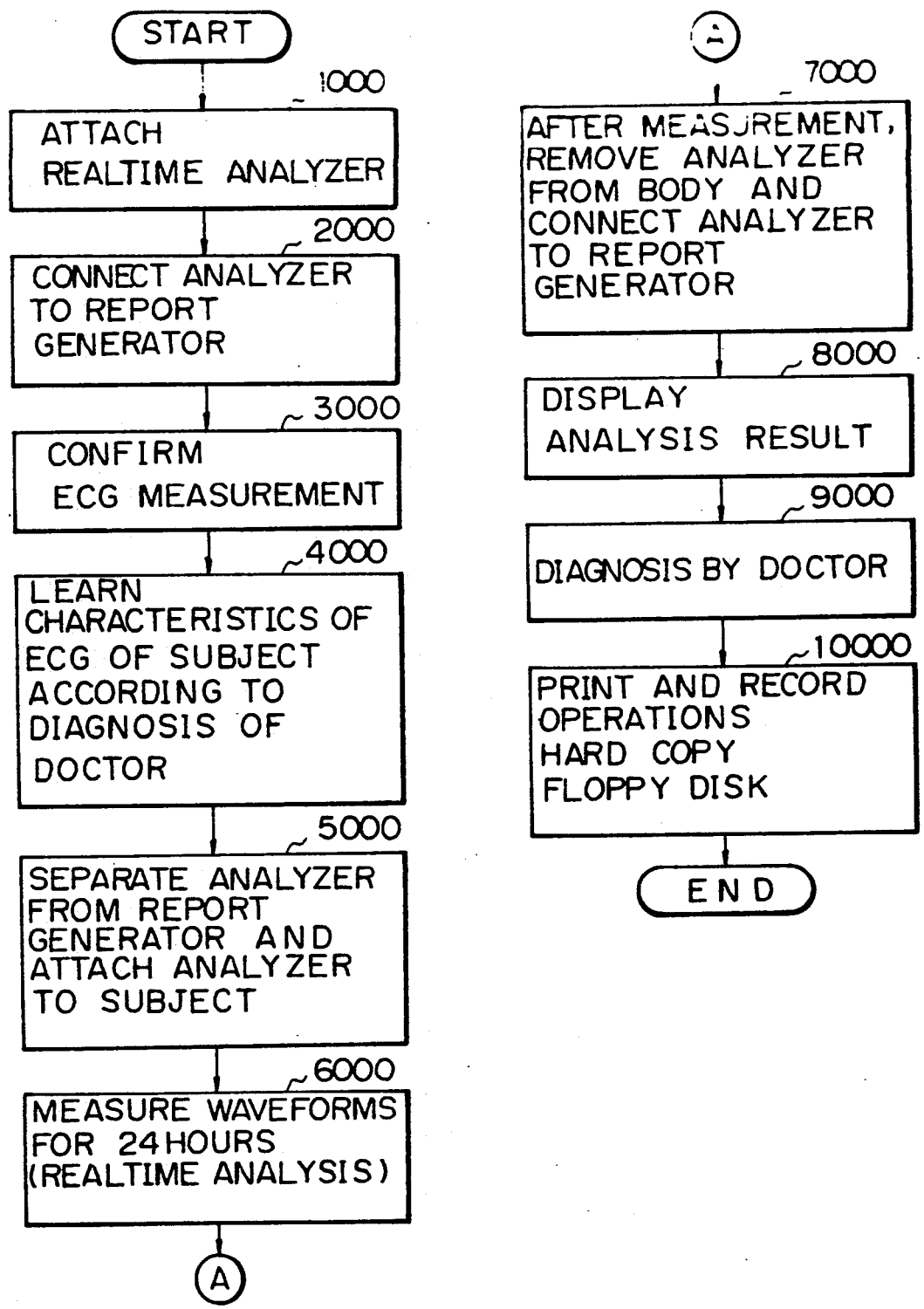
FIG. 9 is a flowchart showing an operation of the apparatuses of FIGS. 2-3.

Returning to the flowchart of FIG. 9, in step 5000, the realtime analyzer 1 is separated from the report generator 2 so as to be mounted on the body of the subject for a long-period ECG waveform measurement.

In step 6000, as shown in FIG. 5, the subject brings about the realtime analyzer 1 through the daily life, for example, for 24 hours so as to conduct a long-term ECG waveform measurement.

The realtime analyzer 1 processes an ECG waveform supplied thereto so as to detect a QRS portion in the QRS detector 12. That is, as described above, in a case where there is found a portion in which the absolute value of the waveform attained by differentiating the ECG waveform exceeds the threshold value TQRS thus learned as described above, a portion of the maximum value of the ECG waveform is recognized as an R peak and a portion of the ECG waveform in a predetermined time width before and after the R peak is identified as the QRS portion.

Next, in the waveform judge section 14, feature values of the QRS portion of the inputted ECG waveform are measured so as to accomplish a realtime analysis on the ECG waveform based on the threshold values set for the feature values selected in the learning process. That is, according to the threshold values set for the feature values selected in the learning process, the judgement is conducted for the normal and abnormal VPB ECG waveforms.

The analysis programs used therefor are stored in the ROM 106 and the RAM 107 of the realtime analyzer 1, namely, the CPU 105 reads these analysis programs from the ROM 106 and the RAM 107 so as to conduct the analysis above. For the QRS portion judged to be an arrhythmia VPB waveform as a result of the analysis, the CPU 105 stores, for example, the judgement of the abnormal waveform and a detection time of the waveform in the RAM 107. As the RAM 107, there is adopted a storage having a capacity capable of storing feature values for the analysis, a result of the analysis, and waveforms judged to be associated with the arrhythmia VPB.

In this fashion, the inputted ECG waveforms are analyzed for 24 hours in a realtime manner so as to judge the normality or the abnormality thereof such that the waveform portions judged to be abnormal are stored for the confirmation to be effected later by a doctor.

The realtime analyzer 1 measures, according to the analysis programs stored in the ROM 106 and the RAM 107, changes with respect to time in the heatbeat of the subject so as to store the data thereof in the RAM 107.

After the long-term ECG measurement and the realtime analysis are completedly achieved for 24 hours, the subject removes the realtime analyzer 1 from the body. The ECG electrodes 101 is also disconnected in this operation. Thereafter the realtime analyzer 1 is connected to the report generator 2.

In step 8000, the report generator 2 receives data from the realtime analyzer 1 so as to generate a report containing the analysis results.

The report of the analysis results efficiently includes the change with respect to time in the heatbeat as shown in FIG. 27a, the time appearance of the abnormal waveform VPB as shown in FIG. 27b, a histogram of the normal waveform, Normal with respect to the R—R interval as shown in FIG. 27c, a histogram of the abnormal waveform, VPB with respect to the R—R interval as shown in FIG. 27d, the abnormal waveform itself as shown in FIG. 27e; furthermore, although not shown, a trend graph in the R—R interval, the frequency of appearances of the abnormal waveforms VPB, and an ST trend graph.

These reports are produced in the microcomputer unit 204 of the report generator 2 so as to be displayed on the display unit 205.

In step 9000, the contents of the report generated by the report generator 2 are displayed on the display unit 205 so as to be checked by the inspector, for example, a doctor for conducting a diagnosis, thereby determining a subsequent action to be taken.

In step 10000, if necessary, the report contents are sent from the microcomputer unit 204 to the printer 207, which prints out the contents as a hardcopy. In addition, the report contents may be stored in a floppy disk 209 of the floppy disk unit 208 or in the hard disk unit 210 for the storage thereof.

Through the processing steps above, the apparatus according to the present embodiment completes the long-term ECG measurement.

According to the embodiment, while effecting a long-term ECG waveform recording for 24 hours, a realtime analysis is achieved on the ECG waveforms so as to produce the results thereof, which in consequence facilitates the analysis to be accomplished after the long-term measurement. That is, it is not necessary to record all waveforms on a magnetic tape and then to reproduce the recorded waveforms, namely, since only the ECG waveforms judged to be abnormal as a result of the realtime ECG waveform analysis are stored, the inspector need only check the waveforms for the confirmation thereof.

In consequence, the storage capacity of the magnetic-tape can be lowered, and hence the size and weight of the realtime analyzer 1 are reduced, which enables the realtime analyzer 1 to be suitable for a portable use.

In addition, if the ECG waveforms of the subject are measured and are analyzed for a predetermined period of time prior to the long-term measurement so that the inspector corrects the analysis results, the personal characteristics of the ECG waveforms of the subject are leared so as to correct the judgement standards of the ECG waveforms to be stored in the realtime analyzer before the long-term measurement is conducted. As a result, the chance of misjudgement associated with the personal characteristics of the subject is minimized in the long-term measurement. In consequence, the chance to miss the abnormal waveform or to mistakenly record a normal waveform as an abnormal waveform is reduced and hence the reliability of the results of the realtime analysis is improved.

Incidentally, according to the embodiment above, four threshold values TQRS, TAQRS, TSQRS, and TTIQRS are set in the step 4010, the measurement is achieved for a predetermined period of time in the step 4020, the detection of the QRS and the judgement of the arrhythmia are conducted in the step 4030, the results are displayed on the display unit 205 in the step 4040, and then the inspector corrects the judgement in the step 4050. However, for these operations above, it may also be possible that without beforehand setting the four threshold values TQRS, TAQRS, TSQRS, and TTIQRS, a measurement is achieved for a predetermined period of time so as to display the measured waveform on the display unit 205, so that the inspector first sets the four threshold values TQRS, TAQRS, TSQRS, and TTIQRS based on the result of the judgement thereof. Next, description will be given of an embodiment in which the ECG waveforms are analyzed in a correlation method (template matching method).

Figure 3A:
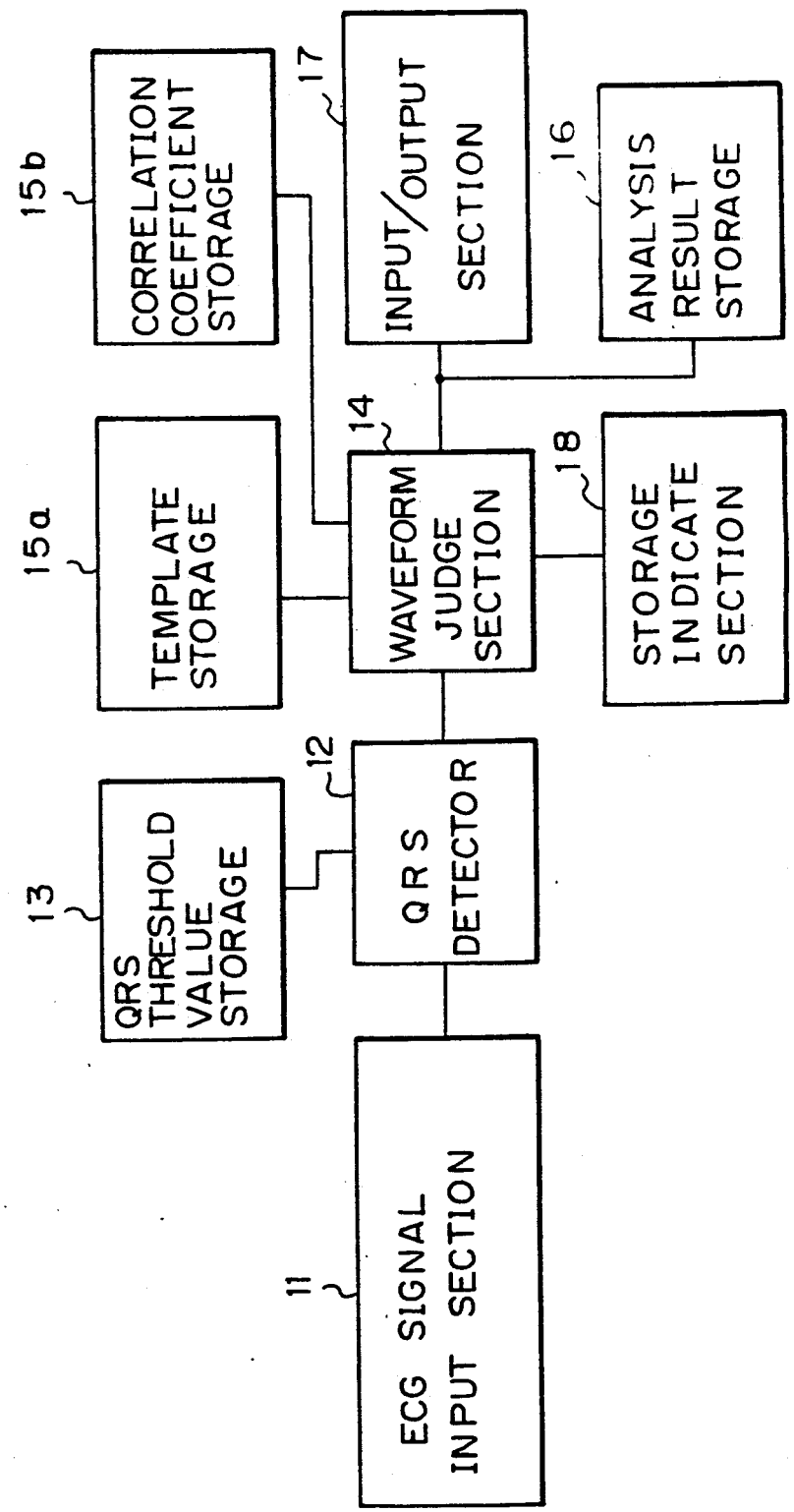
FIGS. 3a-3b are functional block diagrams showing an alternative embodiment in which the present invention is applied to an electrocardiogram measuring apparatus.
Figure 3B:
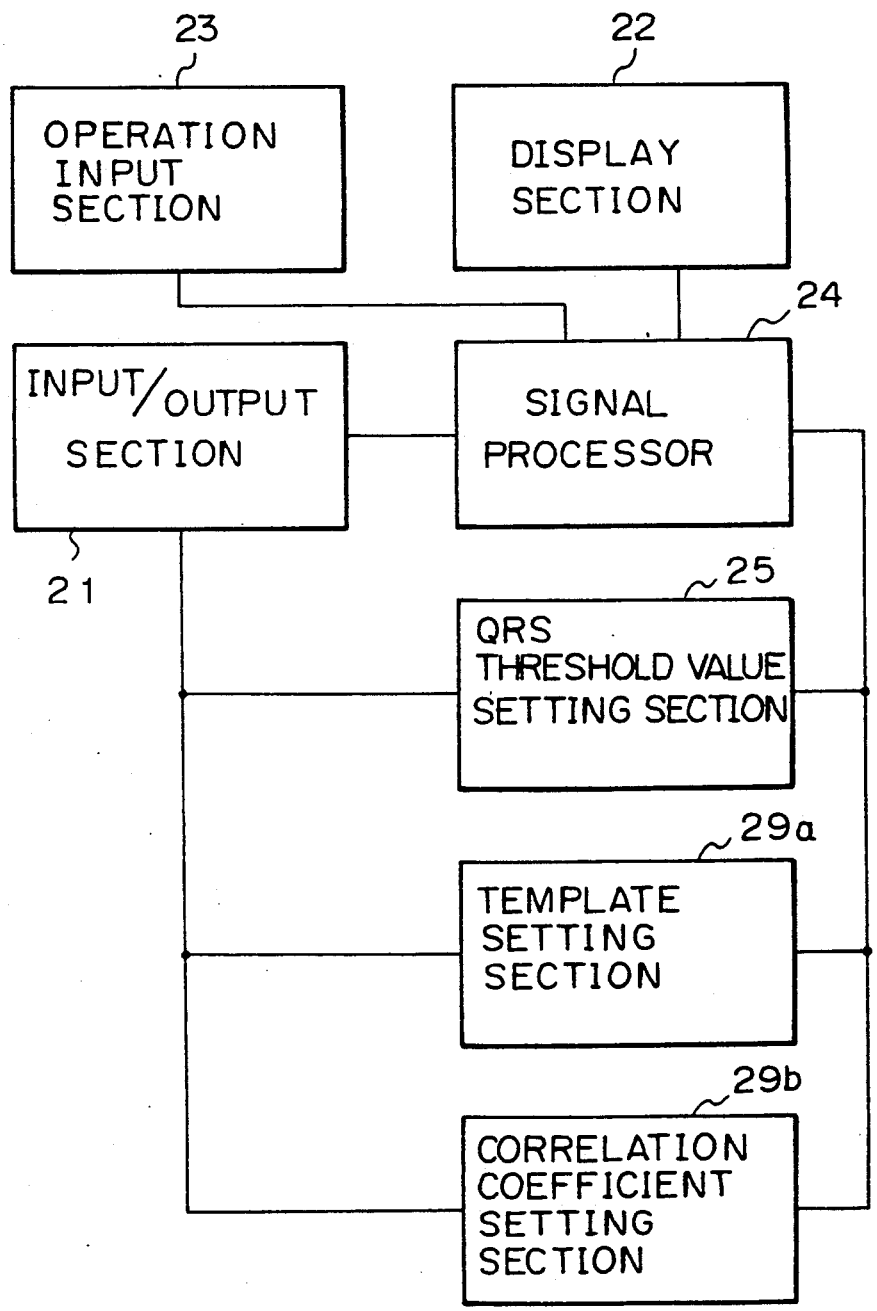

FIGS. 3a-3b are functional block diagrams of an embodiment of an apparatus in which the analysis of the ECG waveforms is conducted according to the correlation method (template matching method).

In this embodiment, there are disposed a template storage 15a and a correlation coefficient storage 15b which are connected to a waveform judge section 14. The template storage 15a is disposed to store therein a template to effect a template matching of an input ECG signal, whereas the correlation coefficient storage 15b is employed to store the correlation coefficients as the standards for the judgement of the matching condition in the template matching.

In addition, there are disposed a template setting section 29a and a correlation coefficient setting section 29b which are connected to a signal processor 24 and an input/output section 21. The template setting section 29a generates a template for the template matching based on the ECG waveforms measured in a predetermined period of time prior to a long-term measurement and the correlation coefficient setting section 29b sets the correlation coefficients for the judgement of the matching condition. Other constitutions are identical to those of FIGS. 2a-2b.

The hardware configuration of the apparatus of FIGS. 3a-3b is the same as that of FIGS. 7-8.

Next, description will be given of the operation of the apparatus according to this embodiment.

Figure 11:
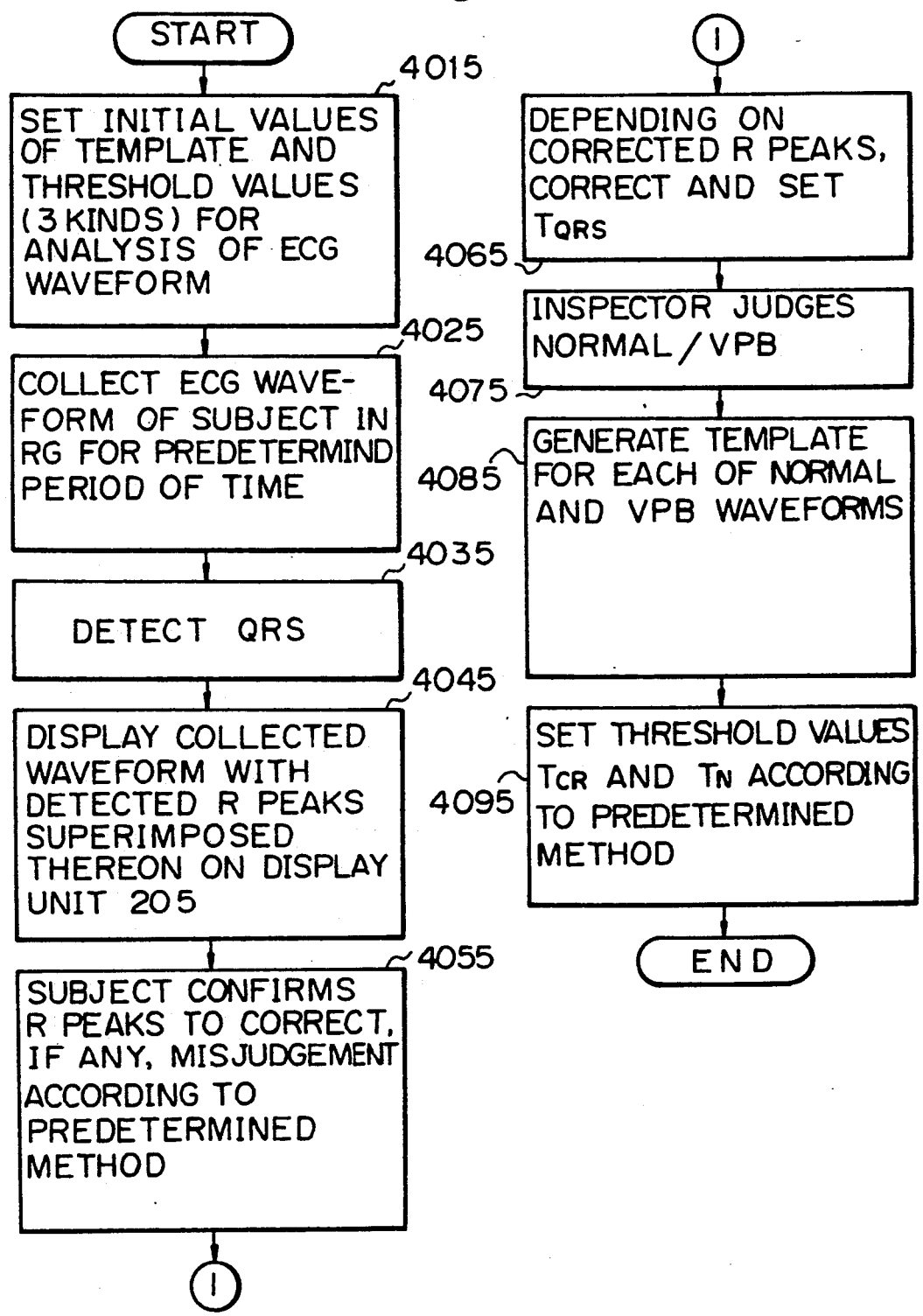
FIG. 11 is a flowchart showing an operation of the learning process of the apparatus of FIG. 3.

Since the operations shown in steps 1000-10000 of FIG. 9 are identical to those of the apparatus which conducts the analysis depending on the feature values, description thereof will be omitted. The learning process will now be described with reference to the flowchart of FIG. 11.

First, in step 4015, for the analysis of ECG waveforms, three threshold values TCR, TN, and TQRS are set in the RAM 107 of the realtime analyzer 1. TQRS is a threshold value to detect a QRS portion as described above. In order to clarify the meanings of TN and TCR, the correlation method will be here described.

In the correlation method also called a template matching method, there are beforehand generated a predetermined number of templates or molds which are waveforms as models with respect to the QRS portions of the ECG waveforms, so that a QRS portion detected in an ECG waveform is compared with the respective templates so as to effect an evaluation thereof depending on the similarity therebetween according to correlation coefficients, thereby judging the presence or absence of the correlation therebetween. Since each template is beforehand associated with a normal waveform or abnormal waveform (arrhythmia), depending on whether the template having a correlation with the detected waveform is normal or abnormal, the QRS portion is judged to be normal or abnormal.

The correlation coefficients are defined by the following formula.

$$Corr_i = \int_D T_i(x) F(X'+x) dx / \sqrt{\int_D T_i^2(x) dx \cdot \int_D F^2(x) dx} \qquad (1)$$

This represents a correlation value of a QRS waveform $F(x)$ for the i-th template $T_i(x)$, where $X'$ and $D$ indicate a matching point and a width of the template, respectively. The value of $CORR_i$ is in the range of $0 \leq CORR_i \leq 1$. For the value of $CORR_i$ having the smaller difference with respect to one, it is assumed that the QRS waveform $F(x)$ has the closer similarity to the template $T_i(x)$ and hence that there exists a correlation therebetween. Usually, an R peak of the QRS portion is set as the matching point such that a fixed width extending before and after this point is adopted to attain $CORR_i$.

Figure 28A:
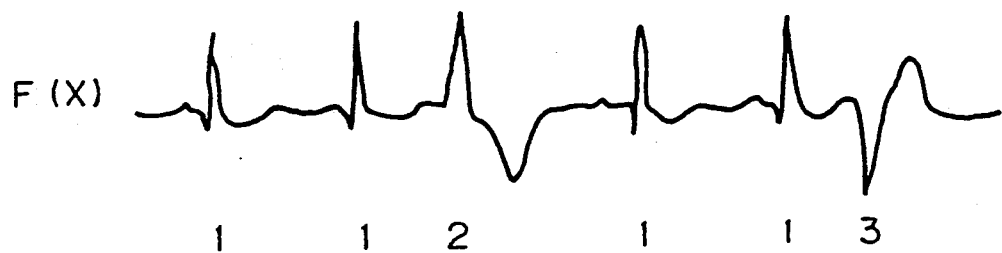
FIGS. 28a-28d is a graph showing an example of the template matching.
Figures 28B, 28C, 28D:
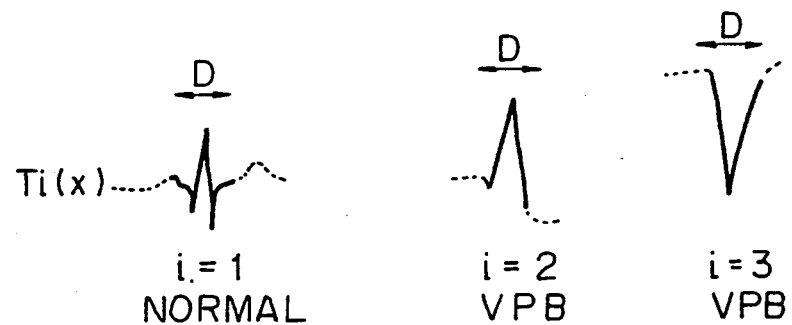

For example, the respective QRS portions of the input signal $F(x)$ shown in FIG. 28a are considered to be correlated with the associated templates $T_i(x)$, $i=1-3$ as indicated therein.

The correlation coefficients $CORR_i$ may also be expressed by use of vectors as follows.

$$CORR_i = \vec{T_i} \cdot \vec{F} / |\vec{T_i}| |\vec{F}| \qquad (2)$$

where, the order of vector corresponds to the width of the template. As can be seen from this expression, the coefficient is obtained by normalizing an inner product of two waveform vectors with respect to norms thereof.

The judgement of the matching, namely, the judgement of whether the template has a correlation with the QRS portion is conducted depending on whether or not the value of $CORR_i$ exceeds a fixed threshold value TCR. That is, an inequality $$CORR_i > TCR$$

is adopted as a condition to judge the matching.

In this expression, for the larger TCR value, the degree of separation is improved so that such a separation is obtained also in a case where the normal and VPB waveforms have a considerable similarity therebetween; however, in this case, for the normal waveform, it is necessary to produce many templates which are slightly and complicatedly different from each other, namely, a lot of templates are required to be prepared. In consequence, there is increased the number of matching trials for the matching judgement or the judgement of whether or not there exists a correlation, which leads to a fear that in a case of a realtime analysis, the analysis processing may be delayed with respect to time. In addition, since there appear many waveforms not having a correlation with such templates beforehand prepared, the judgement of the normality and the abnormality cannot be satisfactorily accomplished. Furthermore, in order to store a lot of templates, there is required a large template area.

In consequence, the threshold value TCR is to be set to the smallest value in a range where the normal waveforms can be discriminated from the VPB waveforms.

In addition, it is also possible to first attain the values of CORRi for all templates such that the presence of the correlation is assumed for the template associated with the greatest CORRi value. Moreover, in a case where the template satisfying the matching condition is absent, the pertinent input waveform is required to be registered as a new template. Next, description will be given of a ratio of norm difference employed as another factor for the judgement of the correlation with the template.

Figure 29:
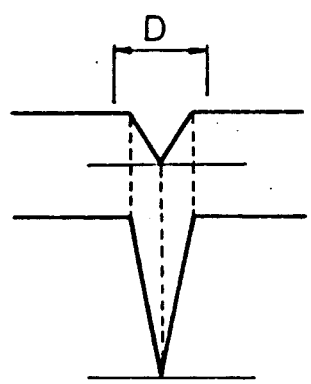
FIG. 29 is a diagram showing relationships of magnification and reduction in the template matching.

When the correlation between an input waveform and a waveform of a template is judged according to the expression (1) or (2), there may possibly occur a case where a matching results between a QRS waveform and a template even if they are clearly different from each other as shown in FIG. 29.

This event takes place, in a case where an expansion/reduction relationship exists along an amplitude direction (a direction of the height) of the waveforms, because the waveforms cannot be separated by use of the expression (1) or (2). That is, for $\vec{F}=a\cdot\vec{T}i$ (where, a is a scalar quantity and $a>0$), CORRi=1 results and hence the separation cannot be implemented.

In order to assuredly effect the separation of such a pattern, it is necessary to achieve a comparison between magnitudes of norms. The ratio of norm difference is defined as follows.

$$DNORM = ABS(|\vec{F}|-|\vec{T}|)/|\vec{T}|$$

As can be seen from this formula, the ratio of norm difference is attained by dividing the absolute value of the difference between the absolute value of the vector of the input waveform F and the absolute value of the vector of the template T by the absolute value of the vector of the template T. For the smaller value of DNORM resulted from this formula, there exists the closer correlation between the input waveform and the template. In consequence, as the condition for the matching judgement, an inequality

DNORM < TN may be employed. That is, when DNORM is less than the threshold value TN, it is assumed that the correlation is present therebetween.

It is favorable for the pattern separation to add the judgement above adopting the ratio of norm difference DNORM to the judgement using the degree of separation CORRi such that the presence of correlation is assumed when the correlation is considered to exist in both judgements.

In a case where the degree of separation CORRi and the ratio of norm difference DNORM are utilized for the correlation judgement, the following formula may be adopted.

$$CORRi = \frac{\vec{Ti}\cdot\vec{F}}{|\vec{Ti}||\vec{F}|} \cdot \left(1 - \frac{ABS(|\vec{F}|-|\vec{Ti}|)}{|\vec{Ti}|}\right)$$

In this expression, the original correlation coefficient CORRi is multiplied by a norm coincidence rate.

In addition, a drift or a shift of the base line is considered as a cause of a meaningless increase in the number of templates. That is, even for QRS waveforms having the same shape, a plurality of templates are respectively produced depending on the magnitude of drift. In order to prevent such a disadvantage, the zero level need only be aligned to the minimum value of the template area.

Returning to FIG. 11, in the step 4015, the general items of the template as described above and the threshold values TCR, TN, and TQRS are initially set in the RAM 107 of the realtime analyzer 1. The threshold values TCR and TN may be set, for example, to 0.90-0.95 and 0.1-0.3, respectively.

Next, in step 4025, ECG waveforms of the subject are measured for a predetermined period of time, for example, one minute to three minutes, favorably, for about five minutes.

Subsequently, like in the case of the operation to effect the analysis depending on the feature values, in step 4035, an R peak is detected by use of the threshold value TQRS, and then in step 4045, the measured ECG waveforms are displayed with indications of detected R peaks superimposed thereon on the display unit 205.

In the next step 4055, the inspector visually checks the ECG waveforms and indications of R peaks displayed on the display unit 205 so as to confirm whether or not the judgement of R peaks are correct, thereby correcting any misjudgement detected. In step 4065, based on the R peaks corrected by the inspector, the QRS threshold value setting section 25 corrects the threshold value TQRS so as to store the corrected value in the QRS threshold value storage 13.

Subsequently, in step 4075, the inspector judges the normality or the abnormality of the ECG waveforms displayed on the display unit 205 so as to input the pertinent data item from the operation input section 23. In step 4085, based on the respective judged waveforms, the template setting section 29a generates templates so as to add the generated templates to those already stored in the template storage 15a. In addition, depending on the judged waveforms, the correlation coefficient setting section 29b corrects the threshold values TCR and TN of the correlation coefficients adopted for the matching judgement in the template matching operation so as to store the corrected values in the correlation coefficient storage 15b.

Thereafter, steps 5000-10000 of FIG. 9 are executed in the similar fashion as for the case associated with the feature value above.

That is, based on the judgement conducted by the inspector, the personal characteristics of the subject is learned such that in a realtime analysis of a long-term measurement, the QRS portions are detected according to the threshold value TQRS corrected depending on the personal characteristics of the subject; furthermore, the template matching is achieved with the corrected threshold values TCR and TN by use of the templates generated according to the personal characteristics of the subject.

In consequence, also in this embodiment, since a realtime analysis of ECG waveforms are conducted while effecting a long-term ECG measurement for 24 hours so as to produce a result thereof, the diagnosis to be achieved after the long-term measurement is facilitated. That is, it is not necessary for the inspector to judge overall contents of the recorded magnetic tape reproduced after the measurement, namely, since only the waveforms judged to be abnormal as a result of the realtime analysis are stored, the inspector need only check the recorded waveforms for the judgement thereof.

In addition, prior to the long-term measurement, a predetermined amount of ECG waveforms of the subject are measured such that the inspector judges the ECG waveforms, so that the personal characteristics of the ECG waveforms of the subject are learned. Based on the learning process, templates to be stored in the realtime analyzer are produced and the threshold values of the correlation coefficients are corrected such that the long-term measurement is conducted by use of the corrected templates and threshold values; in consequence, in the long-term measurement, the chance of misjudgement associated with the personal characteristics of the subject is minimized. As a result, a case where an abnormal waveform is missed or a case where a normal waveform is stored as an abnormal waveform are further prevented and hence the reliability of the results of the realtime analysis is improved.

Incidentally, in the embodiment above, the general values are set in the step 4015 to the templates, the TQRS, and two correlation coefficient threshold values TCR and TN so as to conduct a measurement for a predetermined period of time in the step 4025 such that the QRS portions are detected in the step 4035 to display the result of the detection on the display unit 205 in the step 4045, and the results are judged by the inspector in the step 4055; thereafter, the creation of the templates and the corrections of the threshold values TCR, TN, and TQRS are accomplished. However, in place of these operations above, it may also be possible that without beforehand setting the templates and the threshold values TCR, TN, and TQRS, a measurement is effected for a predetermined period of time so as to display the measured waveforms on the display unit 205 such that based on the judgement conducted by the inspector on the displayed waveforms, the threshold values TCR, TN, and TQRS are set.

In addition, the threshold values TCR, TN, and TQRS initially set in advance may be corrected according to the judgement of the inspector, whereas the templates may be renewed depending on the waveforms obtained after the judgement is conducted by the inspector.

Furthermore, the waveform of the normal QRS portion also varies with a lapse of time during a long-term ECG measurement, and hence it is desirable to accordingly renew the templates.

The renewal of a template is accomplished, for example, by use of the following formula.

$$\vec{T}in = (1 - UR)\vec{T}io + UR \cdot \vec{F}$$

where, $\vec{T}in$ is a new template attained by the renewal, $\vec{T}io$ is an old template before the renewal, and UR stands for a ratio of renewal, which may be set to about 0.1, for example.

Incidentally, although in the description of the embodiment above, the ECG induction is effected in a 1-channel system, the present invention is also applicable to cases associated with the ECG induction using an increased number of channels according to the similar idea. In a case where the number of channels is increased, by use of the method employed in the embodiment above, there need only be accomplished a selection of the QRS characteristic quantities depending on the measurement of the degree of reliability.

According to the present invention, a predetermined amount of organism signals of the subject are measured before a long-term organism signal measurement such that the inspector checks and judges the measured signals so as to effect a learning process on the personal characteristics of the organism signals of the subject, so that the standards for the judgement of the long-term measurement are set depending on the learned characteristics, which hence minimizes the misjudgement associated with the personal characteristics of the subject in the long-term measurement. In consequence, chances to miss an abnormal signal and to store a normal signal as an abnormal signal are reduced and hence the reliability of the results of the realtime analysis is increased.

According to the present invention, since only the ECG waveverms judged to be abnormal as a result of the realtime ECG waveform analysis are stored, the size and weight of the apparatus can be reduced so as to be suitable for a portable use.

Incidentally, the present invention is applicable to cases where organism signals are measured, collected, and analyzed for a long period of time, namely; the present invention is not restricted by the electrocardiogram but is applicable to other items such as a blood pressure waveform and a waveform of brain waves.

We claim:

1. An organism signal measuring apparatus for measuring organism signals of a subject for a predetermined period of time, comprising:

measuring means for measuring the organism signals of the subject for the predetermined period of time, including means for performing realtime analysis on the organism signals to produced results of the analysis according to feature values determining normality and abnormality of the organism signals, and means for storing the results of the analysis and for subsequently outputting the results of the analysis;

measurement control means for receiving the results of the analysis performed by said measuring means during a preliminary period of time, including means for determining feature values of normal and abnormal organism signals measured by said measuring means during the preliminary period of time with evaluation of what is normal and abnormal judged by an inspector, and means for generating a normal histogram and an abnormal histogram for each of the feature values using the organism signals obtained during the preliminary period of time, and means for calculating a degree of separation between the normal histogram and the abnormal histogram for each of the feature values, and means for selecting a judgment feature value having a highest degree of separation among the feature values, and means for determining a threshold value of the judgment feature value depending on the degree of separation of the judgment feature value and means for transferring the threshold value of the judgment feature value to said measuring means for use in a subsequent period of measurement and analysis while said measuring means is disconnected from said measurement control means; and display means for displaying the results of the analysis by said measuring means and the histogram generated by said measurement control means.

2. An organism signal measuring apparatus in accordance with claim 1, wherein the feature values include an area of a QRS portion, a peak value of the ORS portion and a value attained by dividing the area by the peak value.

3. An organism signal measuring apparatus in accordance with claim 2, wherein said measuring means measures electrocardiogram signals as the organism signals, differentiates the electrocardiogram signals to produce differentiation signals and determines a QRS portion in one of the electrocardiogram signals when an absolute value of a corresponding differentiation signal exceeds a predetermined threshold value.

4. An organism signal measuring apparatus for measuring organism signals of a subject for a predetermined period of time, comprising:

measuring means for measuring the organism signals for the predetermined period of time, including means for performing realtime analysis on the organism signals using a template matching method with templates unique to the subject producing the organism signals, to produce results of the analysis, and means for storing the results of the analysis until the predetermined period of time has passed and means for outputting the results of the analysis;

measurement control means for receiving the results of the analysis after the predetermined period of time, and receiving organism signals measured by said measuring means during a preliminary period of time to generate the templates for use in the template matching method using normal and abnormal organism signals with normality determined by an inspector, and means for determining threshold values of correlation coefficients for use in the template matching method, where each correlation coefficient CORRi is calculated for a QRS waveform $\bar{F}$ and a template $\bar{T}i$ as $CORRi = \bar{T}i \cdot \bar{F}/|\bar{T}i||\bar{F}|$ and means for transferring the threshold values of the correlation coefficients to said measuring means prior to separating said measuring means from said measurement control means for the predetermined period of time, said measuring means judging correlation exists between the QRS waveform $\bar{F}$ and the template $\bar{T}i$ when $CORRi > TCR$ where TCR is the threshold value of the correlation coefficient CORRi; and display means for displaying the results of the analysis.

5. An organism signal measuring apparatus in accordance with claim 4, wherein said measuring means determines correlation between the QRS waveform $\bar{F}$ and the template $\bar{T}i$ when $DNORM < Tn$ where $DNORM = ABS(|\bar{F}| - |\bar{T}|)/|\bar{T}|$ and TN is a threshold value of DNORM.

6. An orgnaism signal measuring apparatus for measuring organism signals of a subject for a predetermined period of time, comprising:

measuring means for measuring the organism signals for the predetermined period of time, including means for performing realtime analysis on the organism signals using a template matching method with templates unique to the subject producing the organism signals, to produce results of the analysis, and means for storing the results of the analysis until the predetermined period of time has passed and means for outputting the results of the analysis;

measurement control means for receiving the results of the analysis after the predetermined period of time, and receiving organism signals measured by said measuring means during a preliminary period of time to generate the templates for use in the template matching method using normal and abnormal organism signals with normality determined by an inspector, and means for determining threshold values of correlation coefficients for use in the template matching method, where each said measuring means performing the template matching method using a renewed template $\bar{T}in$ obtained from an old template $\bar{T}io$, a QRS waveform $\bar{F}$ and a renewal rate UR of the template according to $\bar{T}in = (1 - UR)\bar{T}io + UR \cdot \bar{F}$.

7. An organism signal measuring apparatus for measuring and analyzing organism signals of a subject for a predetermined period of time to produce analyzed data, comprising:

input means for inputting the organism signals of the subject;

measuring means for measuring the organism signals input via said input means for a predetermined period of time;

analyzing means for analyzing the organism signals according to feature values derived form the organism signals measured by said measuring means;

analysis data storing means for storing organism signal analysis data unique to the subject producing the organism signals measured by said measuring means, said analyzing means using the organism signal analysis data obtained from organism signals of the subject measured during a previous period of time to obtain feature values of normal and abnormal organism signals with normality judged by an inspector, a normal histogram and an abnormal histogram for each feature value, a degree of separation between the normal and abnormal histograms for each feature value, a feature value having a highest degree of separation selected as a judgement feature value for evaluating the organism signals and a threshold value of the judgement feature value, determined depending on the degree of separation of the judgement feature value, used by said analyzing means to judge the organism signals;

storing means for storing only the organism signals determined by said analyzing means to be abnormal; and output means for outputting the organism signals stored in said storing means after completion of the predetermined period of time.

8. An organism signal measuring apparatus in accordance with claim 7, wherein the feature values include an area of a QRS portion, a peak value of the QRS portion and a value obtained by dividing the area by the peak value.

9. An organism signal measuring apparatus in accordance with claim 8, wherein said analyzing means analyzes electrocardiogram signals as the organism signals, differentiates the electrocardiogram signals to produce differentiation signals and determines a QRS portion in one of the electrocardiogram signals when an absolute value of a corresponding differentiation signal exceeds a predetermined thereshold value.

10. An organism signal measuring apparatus for measuring and analyzing organism signals of a subject for a predetermined period of time to produce analyzed data, comprising:
   input means for inputting the organism signals of the subject;
   measuring means for measuring the organism signals input via said input means for a predetermined period of time;
   analyzing means for analyzing the organism signals, input by said input means, according to a template matching method;
   analysis data storing means for storing organism signal analysis data obtained from the organism signals produced by the subject prior to the predetermined period of time, the organism signal analysis data including templates of normal and abnormal organism signals with normality judged by an inspector and threshold values of correlation coefficients where each correlation coefficient CORRi is calculated from a QRS waveform $\vec{F}$ and a template $\vec{T}i$ according to $CORRI = |\vec{T}i| \cdot |\vec{F}| / |\vec{T}i| |\vec{F}|$, said analyzing means determining correlation between the QRS waveform $\vec{F}$ and the template $\vec{T}i$ when CORRi > TCR where TCR is the threshold value of CORRi;
   storing means for storing only the organism signals determined by said analyzing means to be abnormal; and
   output means for outputtting the organism signals stored in said storing means after completion of the predetermined period of time.

11. An organism signal measuring apparatus in accordance with claim 10, wherein said analyzing means determines correlation between the QRS waveform $\vec{F}$ and the template $\vec{T}i$ when DNORM < TN where $DNORM = ABS(|\vec{F}| - |\vec{T}|)/|\vec{T}|$ and TN is a threshold value of DNORM.

12. An organism signal measuring measuring apparatus for measuring and analyzing organism signals of a subjmect for a predetermined period of time to produce analyzed data, comprising:
   input means for inputting the organism signals of the subject;
   measuring means for measuring the organism signals input via said input means for a predetermined period of time;
   analysis data storing means for storing organism signal analysis data unique to the subject producing the organism signals measured by said measuring means, the organism signal analysis data including templates and thresholds obtained from organism signals measured by said measuring means prior to the predetermined period;
   analyzing means for analyzing the organism signals using the organism signal analysis data by performing a template matching method using a renewed template $\vec{T}in$ obtained from an old template $\vec{T}io$, a QRS waveform $\vec{F}$ and a renewal rate UR of the template according to $\vec{T}in = (1 - UR)\vec{T}io + UR \cdot \vec{F}$;
   storing means for storing only the organism signals determined by said analyzing means to be abnormal; and
   output means for outputting the organism signals stored in said storing means after completion of the predetermined period of time.

* * * * *

UNITED STATES PATENT AND TRADEMARK OFFICE
CERTIFICATE OF CORRECTION

PATENT NO. : 5,092,340

DATED : March 3, 1992

INVENTOR(S) : Yamaguchi et al.

It is certified that error appears in the above-identified patent and that said Letters Patent is hereby corrected as shown below:

Col. 1, line 14, after "measurement" insert --are--;
line 18, "an" (second occurrence) should be --the--;
line 20, "the" should be --an--.

Col. 6, line 41, "ration" should be --ratio--;
line 43 "|$\overline{T1}$" should be --|$\overline{T1}$|--;
line 50, "maching" should be --machining--.

Col. 7, line 56, after "one", should be a new paragraph.

Col. 9, line 32, "23" should be --24--;
line 36, "24" should be --23--;
line 41, after "21" insert --to--.

Col. 11, line 25, "202. Which" should be --202, which--;
line 37, "section" should be --section 21--.

Col. 12, line 45, "latters" should be --letters--.

Col. 13, line 23, "TAQRS" should be --TSQRS--;
line 53, "mix-" should be --max- --.

Col. 14, line 13, "point" should be --points--;
line 31, "he" should be --the--;
line 55, "stroed" should be --stored--;
line 57, "the" (second occurrence) should be --The--;
line 60, "valve" should be --value--.

UNITED STATES PATENT AND TRADEMARK OFFICE
CERTIFICATE OF CORRECTION

PATENT NO. : 5,092,340

DATED : March 3, 1992

INVENTOR(S) : Yamaguchi et al.

It is certified that error appears in the above-identified patent and that said Letters Patent is hereby corrected as shown below:

Col. 15, line 68, "are" should be --area--.

Col. 16, line 1, "AQS" should be --QRS--;
line 30, after "abnormality." should be a new paragraph.

Col. 18, line 10, "N=2" should be --N+2--;
line 16, delete "a".

Col. 22, line 16, "heatbeat" should be --heartbeat--;
line 28, "heatbeat" should be --heartbeat--.

Col. 28, line 30, "waveverms" should be --waveforms--;
line 47, "produced" should be --produce--.

Col 29, line 67 "|$\overline{T}$|" should be --|$\overline{T}$|--;

Signed and Sealed this

Tenth Day of August, 1993

Attest:

MICHAEL K. KIRK

Attesting Officer

Acting Commissioner of Patents and Trademarks